(12) United States Patent
Roy et al.

(10) Patent No.: US 8,716,520 B2
(45) Date of Patent: May 6, 2014

(54) METHOD OF RESOLUTION OF (RS)-1,1'-BI-2-NAPHTHOL FOR OBTAINING ENANTIOMERIC PURE I.E. (S)-(−)-1,1'-BI-2-NAPHTHOL AND/OR (R)-(+)-1,1'-BI-2-NAPHTHOL VIA CO-CRYSTAL FORMATION WITH OPTICALLY ACTIVE DERIVATIVES OF γ-AMINO ACIDS

(75) Inventors: Bhairab Nath Roy, Pune (IN); Girij Pal Singh, Pune (IN); Piyush Suresh Lathi, Pune (IN); Rangan Mitra, Pune (IN)

(73) Assignee: Lupin Limited, Mumbai, Maharashtra (IN)

( * ) Notice: Subject to any disclaimer, the term of this patent is extended or adjusted under 35 U.S.C. 154(b) by 0 days.

(21) Appl. No.: 13/522,141

(22) PCT Filed: Mar. 10, 2010

(86) PCT No.: PCT/IN2010/000141
§ 371 (c)(1),
(2), (4) Date: Jul. 13, 2012

(87) PCT Pub. No.: WO2011/086566
PCT Pub. Date: Jul. 21, 2011

(65) Prior Publication Data
US 2012/0316361 A1    Dec. 13, 2012

(30) Foreign Application Priority Data
Jan. 15, 2010  (IN) ............................... 37/KOL/2010

(51) Int. Cl.
*C07C 229/02*   (2006.01)
*C07C 39/16*    (2006.01)

(52) U.S. Cl.
USPC ......................................... 562/443; 568/719

(58) Field of Classification Search
None
See application file for complete search history.

(56) References Cited

U.S. PATENT DOCUMENTS

| 6,570,036 B1 | 5/2003 | Reuter |
| 2005/0256345 A1 | 11/2005 | Gong et al. |

FOREIGN PATENT DOCUMENTS

| CN | 1097728 | 1/1995 |
| EP | 0 471 498 | 2/1992 |
| JP | 8-245460 | 9/1996 |
| WO | WO 99/12623 | 3/1999 |

OTHER PUBLICATIONS

Aoyagi et al., "Effects of reaction temperature and acyl group for lipase-catalyzed chiral binaphthol synthesis," *Tetrahedron Letters* 47, 2006, pp. 4797-4801.
Bourguignon et al., "Lactone Chemistry, Synthesis of β-Substituted, γ-Functionalized Butanolides and Butenolides and Succinaldehydic Acids from Glyoxylic Acid," *J. Org. Chem.* vol. 46, 1981, pp. 4889-4894.
Bringmann et al., "Bismurrayaquinone A: Synthesis, Chromatographic Enantiomer Resolution, and Stereoanalysis by Computational and Experimental CD Investigations," *Tetrahedron*, vol. 51, No. 34, 1995, pp. 9353-9360.
Brunel et al., "A New and Efficient Method for the Resolution of 1,1'-Binaphthalene-2,2'-diol,"*J. Org. Chem.*, vol. 58, 1993, pp. 7313-7314.
Brunel, "Update 1 of: BINOL: A Versatile Chiral Reagent," *Chem. Rev.*, vol. 107, 2007, pp. PR1-PR45.
Cai et al., "Simple and Efficient Resolution of 1,1'-Bi-2-naphthol," *Tetrahedron Letters*, vol. 36, No. 44, 1995, pp. 7991-7994.
Cavazza et al., "Photochromism in 1,1'-Bi-2-naphthols," *J. Am. Chem. Soc.*, vol. 118, 1996, pp. 9990-9991.
Desiraju, "Crystal and co-crystal," *CrystEngComm*, vol. 5, No. 82, 2003, pp. 466-467.
Du et al., "A new method for optical resolution of BINOL by molecular complexation with (S)-5-oxopyrrolidine-2-carboxanilide," *Tetrahedron Letters*, vol. 43, 2002, pp. 5273-5276.
Egami et al., "Iron-Catalyzed Asymmetric Aerobic Oxidation: Oxidative Coupling of 2-Naphthols," *J. Am.Chem. Soc.*, vol. 131, 2009, pp. 6082-6083.
Etter et al., "The Use of Cocrystallization as a Method of studying Hydrogen Bond Preferences of 2-Aminopyrimidine," *Journal of the Chemical Society, Chemical Communications*, No. 8, 1990, pp. 589-591.
Fabbri et al., "A Widely Applicable Method of Resolution of Binaphthyls: Preparation of Enantiomerically Pure 1,1'-Binaphthalene-2,2'-diol, 1,1'-Binaphthalene-2,2'-diothiol, 2'-Mercapto-1,1'-binaphthalen-2-ol, and 1,1'-Binaphthalene-8,8'-diol," *J. Org. Chem.*, vol. 60, 1995, pp. 6599-6601.
Ha et al., "An economic, practical access to enantiopure 1,1'-binaphthols: enantioselective complexation of threo-(1S,2S)-N-benzyl- N,N-dimethyl[1,3-dihydroxy-1-(4'-nitrophenyl)]-2-propylammonium chloride,"*Tetrahedron:Asymmetry*, vol. 17, 2006, pp. 854-859.
International Search Report from International application No. PCT/IN2010/000141 mailed Aug. 6, 2011.
Juarez-Hernandez et al., "Lipase-catalyzed stereoselective resolution and desymmetrization of binaphthols,"*Tetrahedron: Asymmetry*, vol. 14, 2003, pp. 289-291.
Kamikawa et al., "Stereoselective Synthesis of Axially Chiral Natural Products, (−)-Steganone and O,O '-Dimethylkorupensamine A, Utilizing Planar Chiral (Arene)chromium Complexes," *Tetrahedron*, vol. 56, 2000, pp. 2325-2337.
Kazlauskas, "Resolution of Binaphthols and Spirobiindanols Using Cholesterol Esterase," *J. Am. Chem. Soc.*, vol. 111, 1989, pp. 4953-4959.
Lin et al., "Triple Enantioselection" by an Enzyme-Catalyzed Transacylation Reaction, *Tetrahedron Letters*, vol. 34, No. 38, 1993, pp. 6057-6058.
Pakulski et al., "Separation of Racemic Binaphthol Into Enantiomers. Synthesis of Neomenthylthioacetic Acid Chloride—A New Chiral Resolving Agent," *Tetrahedron: Asymmetry*, vol. 6, No. 1, 1995, pp. 111-114.

(Continued)

*Primary Examiner* — Wu-Cheng Winston Shen
*Assistant Examiner* — Ana Z Muresan
(74) *Attorney, Agent, or Firm* — Merchant & Gould P.C.

(57) ABSTRACT

Novel method for synthesis of optically pure (S)-(−)-1,1'-bi-2-naphthol and/or (R)-(+)-1,1'-bi-2-naphthol via resolution of racemic (RS)-1,1'-bi-2-naphthol through formation of co-crystal with optically active derivatives of γ-amino acids.

8 Claims, 13 Drawing Sheets

(56) References Cited

OTHER PUBLICATIONS

Figure 1:
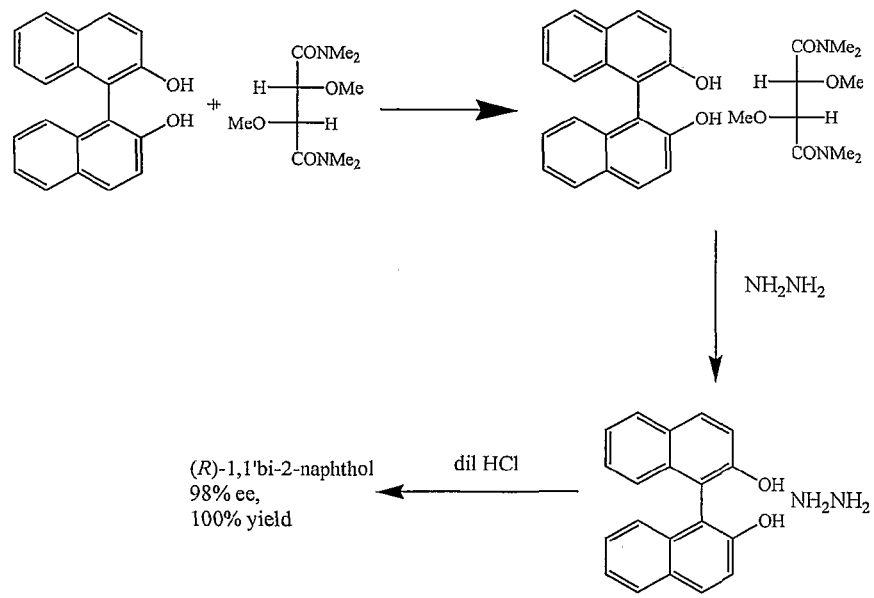

Periasamy et al., "A Simple, Convenient Method for the Resolution of Racemic 2,2'-Dihydroxy-1,1'-Binaphthyl Using (s)-Proline," *Tetrahedron: Asymmetry*, vol. 6, No. 2, 1995, pp. 341-344.

Periasamy et al., "New Methods of Resolution and Enrichment of Enantiomeric Excesses of 1,1'-Bi-2-naphthol," *J. Org. Chem.*, vol. 62, 1997, pp. 4302-4306.

Peroasamy et al., "A New, Convenient Method of Resolution of Racemic 1,1'-Bi-2-naphthol Using Boric Acid and (R)-(+)-α-Methylbenzylamine," *J. Org. Chem.*, vol. 64, 1999, pp. 7643-7645.

Pu, "1,1'-Binaphthyl Dimers, Oligomers, and Polymers: Molecular Recognition, Asymmetric Catalysis, and New Materials," *Chem. Rev.*, vol. 98, 1998, pp. 2405-2494.

Redondo et al., "Use of (S)-BINOL as NMR Chiral Solvating Agent for the Enantiodiscrimination of Omeprazole and its Analogs," *Chirality*, vol. 22, 2010, pp. 472-478.

Roy et al., "A Novel Method for Large-Scale Synthesis of Lamivudine through Cocrystal Formation of Racemic Lamivudine with (S)-(−)-1,1'-Bi(2-naphthol) [(S)-(BINOL)]," *Organic Process Research & Development*, vol. 13, 2009, pp. 450-455.

Shan et al., "A simple, convenient preparation for enantiomerically pure 1,1'-bi-2-naphthols," *Tetrahedron: Asymmetry*, vol. 9, 1998, pp. 3985-3989.

Sridhar et al., "Novel Horseradish Peroxidase Catalysed Enantioselective Oxidation of 2-Naphthols to 1,1'- Binaphthyl-2,2'-diols," *Tetrahedron Letters*, vol. 38, No. 32, 1997, pp. 5695-5696.

Takemoto et al., "Enantioselective oxidative coupling of 2-naphthol derivatives catalyzed by *Camellia sinensis* cell culture," *Tetrahedron Letters*, vol. 43, 2002, pp. 8499-8501.

Tamai et al., "A Practical Method for Resolution for the Optical Isomers of 2,2'-Dihydroxy-1,1'-binaphthalene," *Synthesis Papers*, 1990, pp. 222-223.

Toda et al., "Mutual Optical Resolution of 2,2'-Dihydroxy-1,1'-Binaphthyl and Alkyl Aryl or Dialkyl Sulfoxides by Complex Formation," *Tetrahedron Letters*, vol. 25, No. 43, 1984, pp. 4929-4932.

Toda et al., "Efficient Optical Resolution of 2,2'-Dihydroxy-1,1'-binaphthyl and Related Compounds by Complex Formation with Novel Chiral Host Compounds Derived from Tartaric Acid," *J. Org. Chem.*, vol. 53, 1988, pp. 3607-3609.

Toda et al., "Oxidative Coupling Reactions of Phenols with $FeCl_3$ in the Solid State," *J. Org. Chem.*, vol. 54, 1989, pp. 3007-3009.

Toda et al., "Optical Resolution of Binaphthyl and Biphenanthryl Diols by Inclusion Crystallization with *N*-Alkylcinchonidium Halides. Structural Characterization of the Resolved Materials," *J. Org. Chem.*, vol. 59, 1994, pp. 5748-5751.

Venkatraman et al., "A Novel, Simple Method for Enrichment of Enantiomeric Excess of Scalemic 1,1'-Bi-2-naphthol," *Tetrahedron: Asymmetry*, vol. 7, No. 9, 1996, pp. 2471-2474.

Vishweshwar et al., "Pharmaceutical Co-Crystals," *Journal of Pharmaceutical Sciences*, vol. 95, No. 3, 2006, pp. 499-516.

Wang et al. "Diastereoselective Synthesis of 1,1'-Binaphthyl-2,2'-diol," *J. Org. Chem.*, vol. 60, 1995, pp. 7364-7365.

Yoshizawa et al., "Enantiomer separation of rac-2,2'-dihydroxy-1,1'-binaphthyl (BNO) by inclusion complexation with racemic or achiral ammonium salts and a novel transformation of a 1:1:1 racemic complex of BNO, $Me_4N^+ \cdot Cl^-$ and MeOH into conglomerate complex in the solid state," *Tetrahedron*, vol. 60, 2004, pp. 7767-7774.

Zi-xing et al., "A Convenient Preparation of Enantiopure 1,1'-bi-2naphthols via an Inclusion Complexation in the Solid State," *Wuhan University Journal of Natural Sciences*, vol. 5, No. 4, 2000, pp. 469-473.

METHOD OF RESOLUTION OF (RS)-1,1'-BI-2-NAPHTHOL FOR OBTAINING ENANTIOMERIC PURE I.E. (S)-(−)-1,1'-BI-2-NAPHTHOL AND/OR (R)-(+)-1,1'-BI-2-NAPHTHOL VIA CO-CRYSTAL FORMATION WITH OPTICALLY ACTIVE DERIVATIVES OF γ-AMINO ACIDS

This application is a National Stage Application of PCT/IN2010/000141, filed 10 Mar. 2010, which claims benefit of Serial No. 37/KOL/2010, filed 15 Jan. 2010 in India and which applications are incorporated herein by reference. To the extent appropriate, a claim of priority is made to each of the above disclosed applications.

FIELD OF INVENTION

The invention relates to novel method for synthesis of optically pure (S)-(−)-1,1'-bi-2-naphthol and/or (R)-(+)-1,1'-bi-2-naphthol via resolution of racemic (RS)-1,1'-bi-2-naphthol through formation of co-crystal with optically active derivatives of γ-amino acids.

BACKGROUND OF THE INVENTION 1,1'-bi-2-naphthol [CAS. No 602-09-05] [I] is one of the industrially important chemicals and is produced in large quantities all over the world.

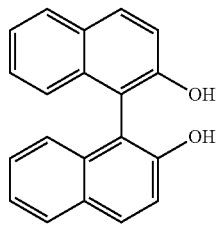

[I]

1,1'-bi-2-naphthol occurs in two optically active forms because of its restricted rotation viz. (S)-(+1,1'-bi-2-naphthol [CAS No. 18531-99-2] and (R)-(+)-1,1'-bi-2-naphthol [CAS No. 18531-94-7].

(S)-(−)-1,1'-bi-2-naphthol and (R)-(+)-1,1'-bi-2-naphthol are generally obtained by resolution of racemic i.e. (RS)-1,1'-bi-2-naphthol, which is synthesized by oxidative coupling of 2-naphthol in presence of transition metal salts having variable valence such as $FeCl_3$, $CuSO_4$, $CuCl_2$, $VO^{++}$ complex, etc. (J. Org. Chem. 1989, 54, 1252)

Both the optically pure (S)-(+1,1'-bi-2-naphthol and (R)-(+)-1,1'-bi-2-naphthol have wide applications in synthetic chemistry and are used as building blocks for the synthesis/manufacture of many important chemicals including natural products, (Tetrahedron 1995, 51, 9353; Tetrahedron 2000, 56, 2325); and also as chiral auxiliaries in stoichiometric quantity as well as in catalytic amount in various asymmetric syntheses.

The optically pure (S)-(−)-1,1'-bi-2-naphthol and (R)-(+)-1,1'-bi-2-naphthol are used as auxiliary or converted to specific chiral ligands for use in various asymmetric reactions, such as, enantioselective reduction, in various catalytic asymmetric Diels-Alder reactions, ene reactions, asymmetric Michael additions, alkylations, oxidations, epoxidations and nitroaldol reactions etc. (Chem. Rev. 1998, 98, 2405-2494; Chem. Rev. 2007, 107, PR1-PR45).

Recently, it has also been demonstrated that optically active 1,1'-bi-2-naphthol can also be used for optical resolution of active pharmaceutical compounds such as omeprazole, lamivudine etc. (OPRD, 2009, 13, 450-455) and as a chiral shift reagent for the determination of the optical purity and absolute configuration of a wide range of chiral compounds (Chirality, 2009).

The synthesis of enantiomerically pure (R) or (S)-1,1'-bi-2-naphthol has been extensively studied with essentially two major approaches such as resolution (enzymatic and chemical) and, asymmetric synthesis.

I) Enzymatic Resolution:

Kazlaukas has reported cholesterol esterase catalyzed enantioselective hydrolysis of binaphthol esters. The reported method requires an additional step for preparation of binaphthol esters but unfortunately the said enzyme is not commercially available. (J. Am. Chem. Soc., 1989, 111, 4953)

Enantioselective trans-esterification reaction of rac-1-indanol with rac-1,1'-binaphthyl-2-2-dibutyrate in presence of enzymes such as procine pancreatic lipase, procine pancreatin and cholesterol esterase have been reported. This method has been demonstrated for mutual separation of rac-1-indanol and racemic (RS)-1,1'-bi-2-naphthol but overall yield for optically pure 1,1'-bi-2-naphthol is low and needs an additional step for separation. Hence, this could not be an industrial process for obtaining optically pure 1,1'-bi-2-naphthol (Tetrahedron Lett. 1993, 34, 6057).

Enantioselective monomethyl etherification of racemic (RS)-1,1'-bi-2-naphthol in presence of bovine serum albumin has demonstrated low enantiomeric excess. (J. Am. Chem. Soc., 1996, 118, 9990)

Lipase catalyzed resolution of (RS)-1,1'-bi-2-naphthol has also reported low enantiomeric excess. The reported method needs an additional step for preparation of binaphthol esters. (Tetrahedron: Asymmetry 2003, 14, 289; Tetrahedron Lett. 2006, 47, 4797)

It is evident from the above that in enzymatic resolution methods, more often than not, the separation is not economic and also enzymes are not available commercially. Further, overall cost for obtaining optically pure 1,1'-bi-2-naphthol through enzymatic resolution is very high. Although, commercially available enzymes such as lipases are used for enantioselective hydrolysis of 1,1'-bi-2-naphthol ester, enantiomeric excess is far from desirable.

Asymmetric oxidative coupling is scientifically interesting and demonstrated by using *Camellia sinensis* cell culture or horseradish peroxidase. However, enantiomeric excess is far from satisfactory (Tetrahedron Lett. 2002, 43, 8499; Tetrahedron Lett. 1997, 38, 5695)

II) Chemical Resolution:

Resolution of (RS)-1,1'-bi-2-naphthol via formation of diastereomeric inclusion complexes with various chiral hosts is very well documented. Some of these methods reportedly gave low enantiomeric excess. Furthermore, in many cases overall yield is low thus rendering most methods economically unfeasible.

More details about literature methods are discussed hereinafter.

Chiral amide derivatives of succinic acid and tartaric acid are used for resolution of (RS)-1,1'-bi-2-naphthol. In the said method, synthesis of chiral amide derivatives is tedious and requires $POCl_3$. Furthermore to obtain optically pure 1,1'-bi-2-naphthol from complex needs an additional step of forming complex with aqueous $NH_2NH_2$ followed by decomposition in presence of dilute hydrochloric acid (J. Org. Chem. 1988, 53, 3607-3609). FIG. 1 gives the schematic representation of resolution of (RS)-1,1'-bi-2-naphthol via amide derivatives of tartaric acid.

Resolution of (RS)-1,1'-bi-2-naphthol by forming inclusion complex with chiral cinchonidium halides such as N-benzylcinchonidium and n-butyl cinchonidium bromide (Tetrahedron Lett. 1995, 36, 7991-7994; J. Org. Chem. 1994, 59, 5748-5751), chiral 1,2-diaminocyclohexane (EP 471498), chiral m-tolyl methyl sulfoxide (Tetrahedron Lett. 1984, 25, 4929-4932) are not at all cost effective processes at industrial scale.

Resolution of (RS)-1,1'-bi-2-naphthol by forming inclusion complex with L-proline (Tetrahedron: Asymmetry, 1995, 6, 341-344); (R)-(α)-methyl benzylamine (J. Org. Chem. 1999, 64, 7643-7645); (R)-2-aminobutanol (Synthesis 1990, 3, 222-223); (S)-5-oxopyrrolidine-2-carboxanilide (JP 08245460, Tetrahedron Lett. 2002, 43, 5273-5276) have demonstrated poor enantiomeric excess and in most of these cases, overall yield is very low. Hence, they cannot be used as an industrial process for obtaining optically pure 1,1'-bi-2-naphthol.

Figure 2:
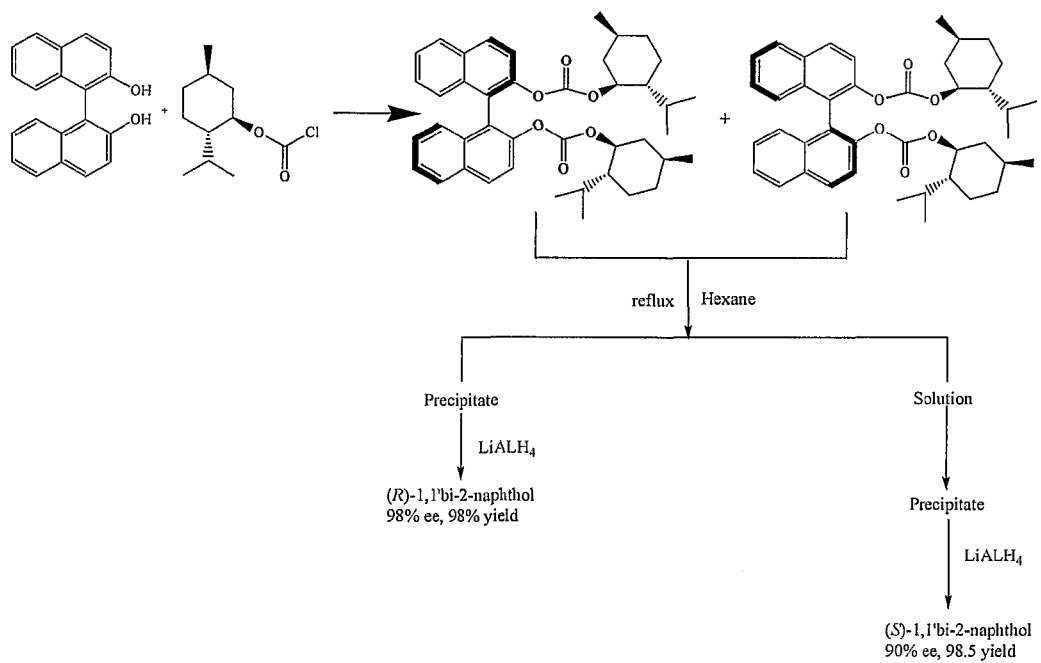

Resolution of (RS)-1,1'-bi-2-naphthol is also demonstrated by reaction with (R)-menthyl chloroformate (J. Org. Chem., 1995, 60, 6599-6601); neomenthylthioacetic acid chloride (Tetrahedron: Asymmetry 1995, 6, 111-114) and separation of diastereomers by crystallization. However, lithium aluminum hydride, a hazardous chemical, is used to decompose the complex, which is not operation friendly to handle at large scale. Hence it cannot be used as an industrial process for obtaining optically pure 1,1'-bi-2-naphthol. Moreover, cost per unit kg of final product is also high. FIG. 2 gives the schematic representation of resolution of (RS)-1,1'-bi-2-naphthol via (R)-menthyl chloroformate.

Figure 3:
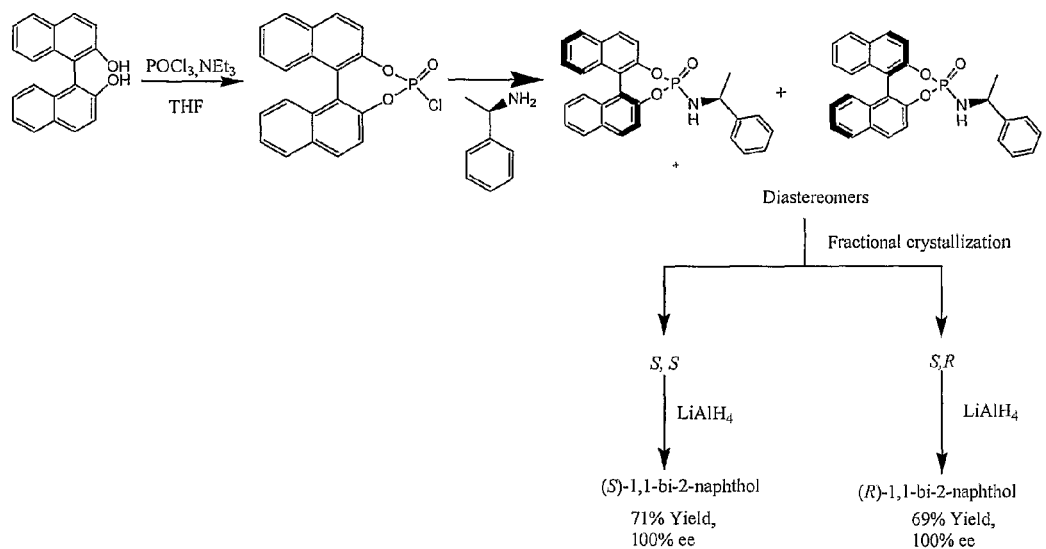

(III) Formation of Phosphate Ester Diastereomeric Inclusion Complexes:

Resolution of (RS)-1,1'-bi-2-naphthol is also demonstrated by forming phosphate ester of (RS)-1,1'-bi-2-naphthol followed by diastereomeric complex with optically pure α-methylbenzylamine (J. Org. Chem. 1995, 60, 7364-7365) or L-menthol (J. Org. Chem. 1993, 58, 7313-7314), which is further separated by crystallization. Above said methods use LiAlH$_4$, which is not environmentally benign and require special handling conditions. Hence it cannot be used as an industrial process for obtaining optically pure 1,1'-bi-2-naphthol. FIG. 3. gives the schematic representation of resolution of (RS)-1,1'-bi-2-naphthol via phosphate ester diastereomeric complex with chiral α-methyl benzyl amine.

Figure 4:
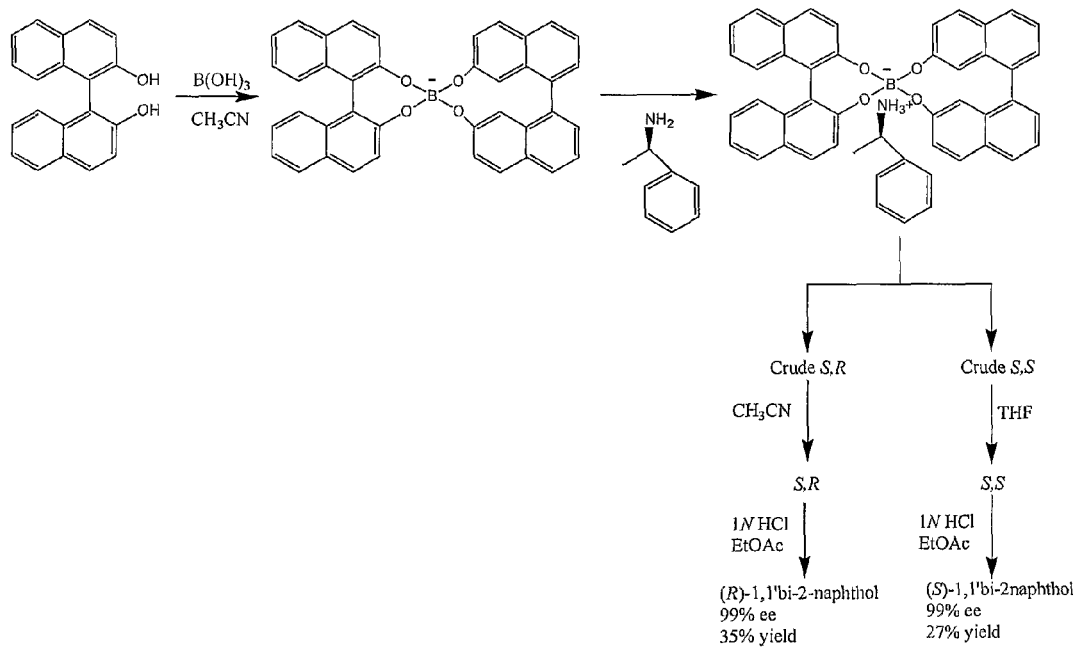

(IV) Formation of Borate Ester Diastereomeric Inclusion Complexes:

Resolution of (RS)-1,1'-bi-2-naphthol is also demonstrated by forming borate ester of (RS)-1,1'-bi-2-naphthol and further treating with (R)-α-methylbenzylamine (J. Org. Chem. 1999, 64, 7643-7645); quinine (CN 1097728); TMEDA (Tetrahedron: Asymmetry 1996, 7, 2471-2474) or L-Proline to obtain diastereomeric complex (Tetrahedron: Asymmetry 1998, 9, 3985), which is subsequently separated by crystallization. Most of the above methods have demonstrated poor enantiomeric excess and overall yield is also very low. Hence these cannot be used as industrial processes for obtaining optically pure 1,1'-bi-2-naphthol. FIG. 4. represents the schematic representation of the resolution of (RS)-1,1'-bi-2-naphthol via borate ester complex.

(V) Conglomerate Separation:

Toda et al., reported the process for resolution of (RS)-1,1'-bi-2-naphthol through inclusion complex formation with racemic or achiral ammonium salts and transformation of complex into a conglomerate (Tetrahedron, 60, 2004; 7767-7774). WO 99/12623 describes the process for separation of (RS)-1,1'-bi-2-naphthol by forming inclusion complex with N-methylpyrrolidine and subsequent conglomerate separation.

VI) Asymmetric Synthesis:

US Patent 2005/0256345 describes the process for asymmetric oxidative coupling of 2-naphthol in presence of vanadium complex. Egami and Katsuki have reported iron catalyzed asymmetric aerobic oxidative coupling of 2-naphthol (J. Am. Chem. Soc. 2009, 131, 6082-6083). Rate of reaction of vanadium complex based asymmetric oxidation is very slow whereas iron catalyzed asymmetric coupling reports poor enantiomeric excess.

U.S. Pat. No. 6,570,036 describes the co crystallisation process for separation of racemic naphthylethyl amine with (S)-ibuprofen and (S)-diacetone ketogulonic acid. However, there is no embodiment of single crystal data, Powder X-ray diffraction analysis and hydrogen bond interaction pattern for co-crystal.

It is evident from prior art that there is a need for an eco-friendly, "green", cost effective, easy-to-operate industrial-scale synthesis of optically pure compound viz. (S)-(−)-1,1'-bi-2-naphthol and (R)-(+)-1,1'-bi-2-naphthol.

This invention provides that.

SUMMARY OF INVENTION

The present invention is directed towards the method for preparation of enantiomerically pure (S)-(+1,1'-bi-2-naphthol and (R)-(+)-1,1'-bi-2-naphthol from (RS)-1,1'-bi-2-naphthol (I) through formation of co-crystal with sequential addition of desired optically pure γ-amino acid derivatives.

Co-crystal is defined as a crystal that contains two different molecules as a complex held together by H-bonds, π-stacking or van der Waals forces (both molecules are solids at ambient temperature) and co-crystal design such as crystal engineering and supramolecular chemistry define it as consequence of molecular recognition events between different molecular species (J. Pharm Sci 2006, 95, 499-516; Crystal Engg. Commun, 2003, 5, 466-67; J. Chem. Soc: Chem. Comm. 1990, 589-591).

The method of manufacturing essentially consists of addition of a particular pure diastereomer of 3-[(1-phenyl ethylamino)-methyl]hexanoic acid to a mixture of racemic (RS)-1,1'-bi-2-naphthol [I] in methanol, wherein only one form of enantiomerically pure 1,1'-bi-2-naphthol forms a 1:1 co-crystal with the said optically pure γ-amino acid derivative. The co-crystal thus formed crystallizes out leaving the other antipode of 1,1'-bi-2-naphthol in the mother liquor. Said co-crystal is then clarified from the mother liquor by using techniques known in the art like filtration, centrifugation, decantation etc.

The mother liquor, which contains the other antipode of 1,1'-bi-2-naphthol, is treated with the other antipode of optically pure γ-amino acid derivative to form a similar 1:1 co-crystal.

The co-crystal is then decomposed with a hydrogen ion source like a Brønsted acid such as dilute hydrochloric acid, dilute sulfuric acid, acetic acid etc. to obtain optically pure 1,1'-bi-2-naphthol. γ-amino acid is recovered by neutralizing the acid aqueous solution with sodium bicarbonate and reused, thereby making the whole process very cost effective and easily operable.

When (RS)-1,1'-bi-2-naphthol [I] is reacted with (S,S)-3-[(1-phenyl ethyl amino)-methyl]-hexanoic acid [II],

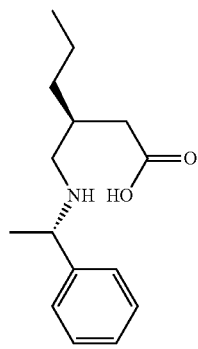

[II]

there is formation of the easily separable co-crystal with (S)-(−)-1,1'-bi-2-naphthol, which is separated by filtration, leaving behind (R)-(+)-1,1'-bi-2-naphthol in mother liquor.

Further, mother liquor is reacted with (R,R)-3-[(1-phenyl ethylamino)-methyl]-hexanoic acid [III],

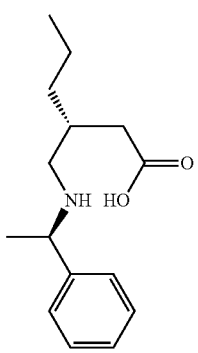

[III]

which forms the easily separable co-crystal with (R)-(+)-1,1'-bi-2-naphthol and is separated by filtration.

The co-crystals thus obtained i.e. (S,S)-3-[(1-phenyl ethylamino)-methyl]-hexanoic acid: (S)-(−)-1,1'-bi-2-naphthol [IV] and (R,R)-3-[(1-phenyl ethylamino)-methyl]-hexanoic acid: (R)-(+)-1,1'-bi-2-naphthol [V] are treated separately with dilute hydrochloric acid to obtain (S) and (R) optically pure 1,1'-bi-2-naphthol respectively. The % ee of the (R)-(+)-1,1'-bi-2-naphthol and (S)-(−)-1,1'-bi-2-naphthol have been found to be min of 99%.

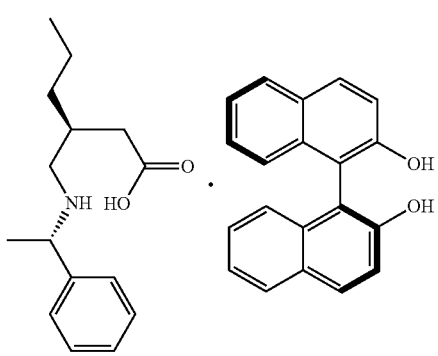

[IV]

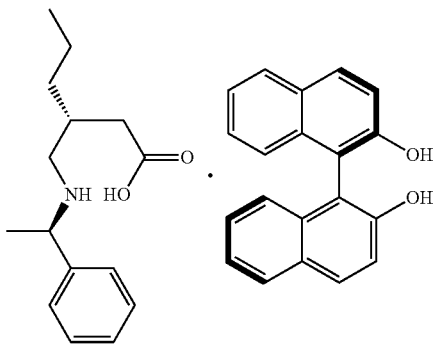

[V]

Single crystal X-ray diffraction pattern analysis of co-crystal (S,S)-3-[(1-phenyl ethylamino)-methyl]-hexanoic acid: (S)-(−)-1,1'-bi-2-naphthol [IV] shows that the composition is 1:1.

When (RS)-1,1'-bi-2-naphthol is reacted with (R,S)-3-[(1-phenyl ethylamino)-methyl]-hexanoic acid [VI],

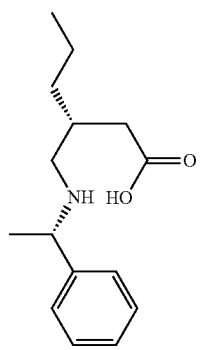

[VI]

there is formation of the easily separable co-crystal with (S)-(−)-1,1'-bi-2-naphthol which is separated by filtration, leaving behind (R)-(+)-1,1'-bi-2-naphthol in the mother liquor.

Further, mother liquor (filtrate) is reacted with (S,R)-3-[(1-phenyl ethylamino)-methyl]-hexanoic acid [VII],

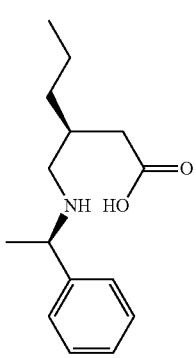

[VII]

which forms the easily separable co-crystal with (R)-(+)-1,1'-bi-2-naphthol and is separated by filtration.

The co-crystals thus obtained i.e. (R,S)-3-[(1-phenyl ethylamino)-methyl]-hexanoic acid: (S)-(−)-1,1'-bi-2-naphthol [VIII] & (S,R)-3-[(1-phenyl ethyl amino)-methyl]-hexanoic acid: (R)-(+)-1,1'-bi-2-naphthol [IX] are treated with dilute hydrochloric acid to obtain (S)-(−)-1,1'-bi-2-naphthol and (R)-(+)-1,1'-bi-2-naphthol respectively. The % ee of the (R)-(+)-1,1'-bi-2-naphthol and (S)-(−)-1,1'-bi-2-naphthol have been found to be min of 95%.

(VIII)

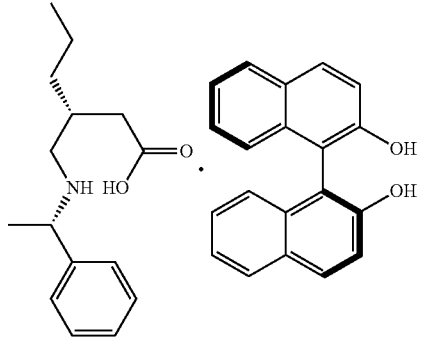

(IX)

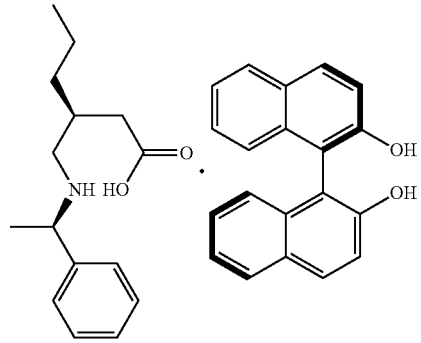

Single crystal X-ray diffraction pattern analysis of co-crystal (R,S)-3-[(1-phenyl ethylamino)-methyl]-hexanoic acid: (S)-(−)-1,1'-bi-2-naphthol [VIII] shows that the composition is 1:1.

BRIEF DESCRIPTION OF ACCOMPANYING DRAWINGS

Figure 5:
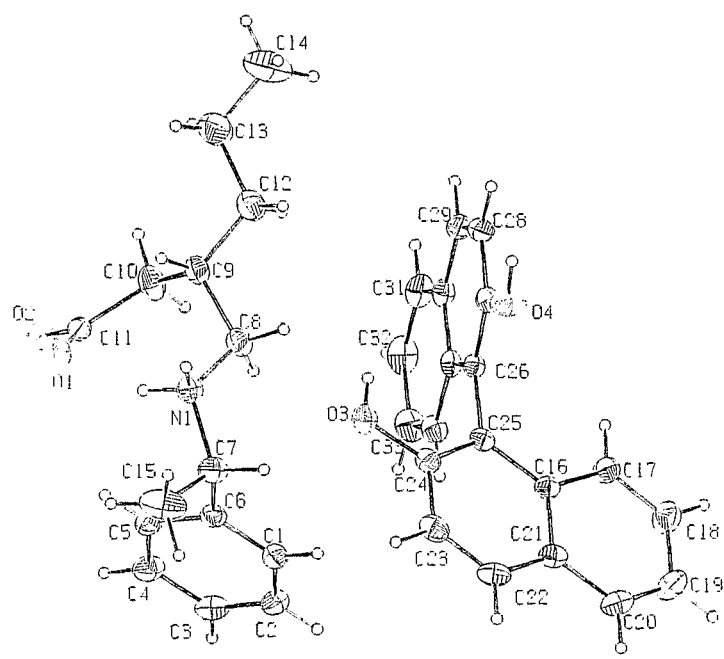

FIG. 1: Schematic representation of resolution of (RS)-1,1'-bi-2-naphthol via amide derivatives of tartaric acid FIG. 2: Schematic representation of resolution of (RS)-1,1'-bi-2-naphthol via (R)-menthyl chloroformate FIG. 3: Schematic representation of resolution of (RS)-1,1'-bi-2-naphthol via phosphate ester diastereomeric complex with chiral (a)-methyl benzyl amine FIG. 4. Schematic representation of the resolution of (RS)-1,1'-bi-2-naphthol via borate ester complex FIG. 5: ORTEP diagram of the single crystal of the co-crystal [IV]

Figure 6:
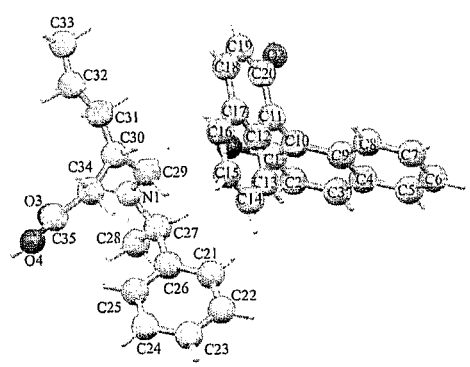

FIG. 6: Diagram of the single crystal of the co-crystal [VIII]

Figure 7:
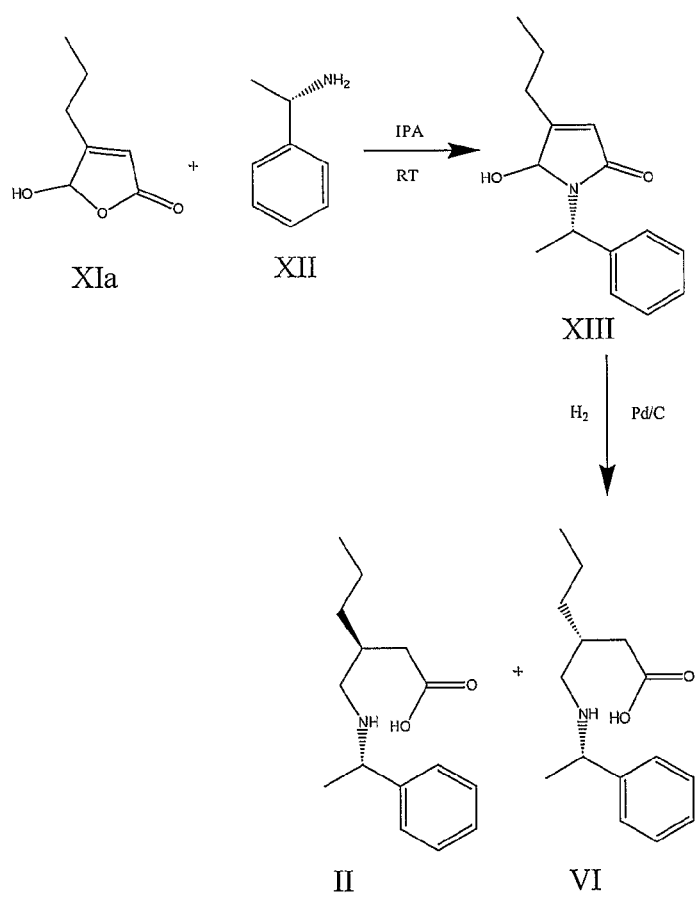

FIG. 7. Schematic representation of synthesis of compound [II] and [VI]

Figure 8:
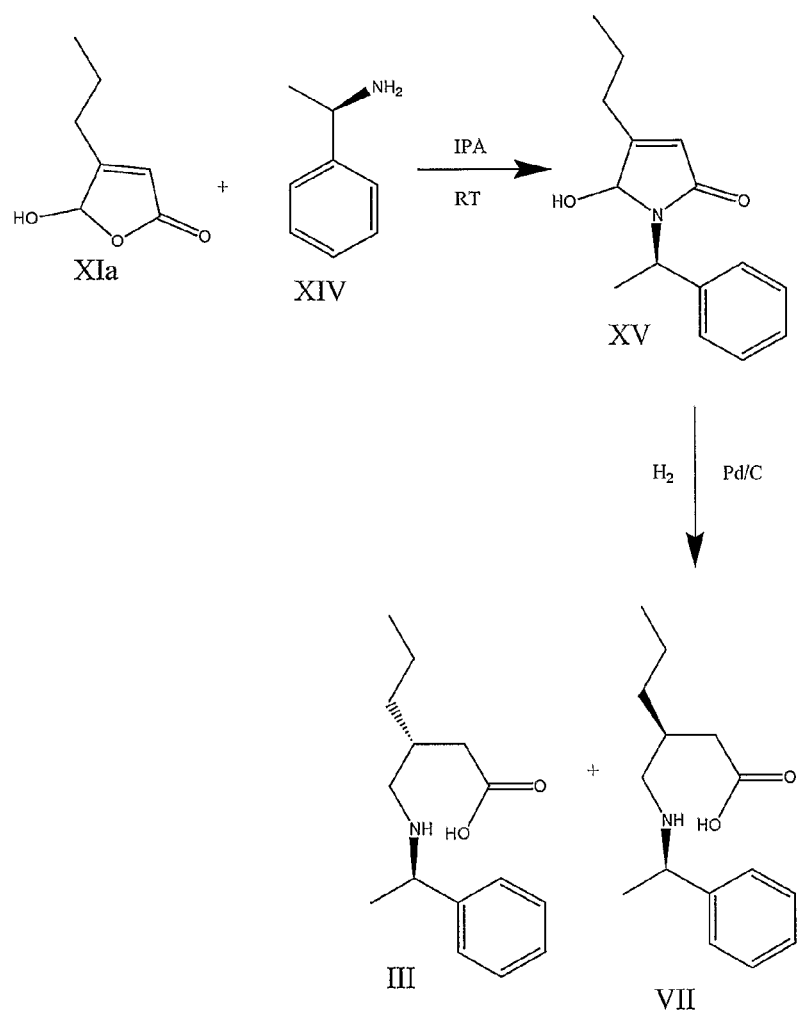

FIG. 8. Schematic representation of synthesis of compound [III] and [VII]

Figure 9:
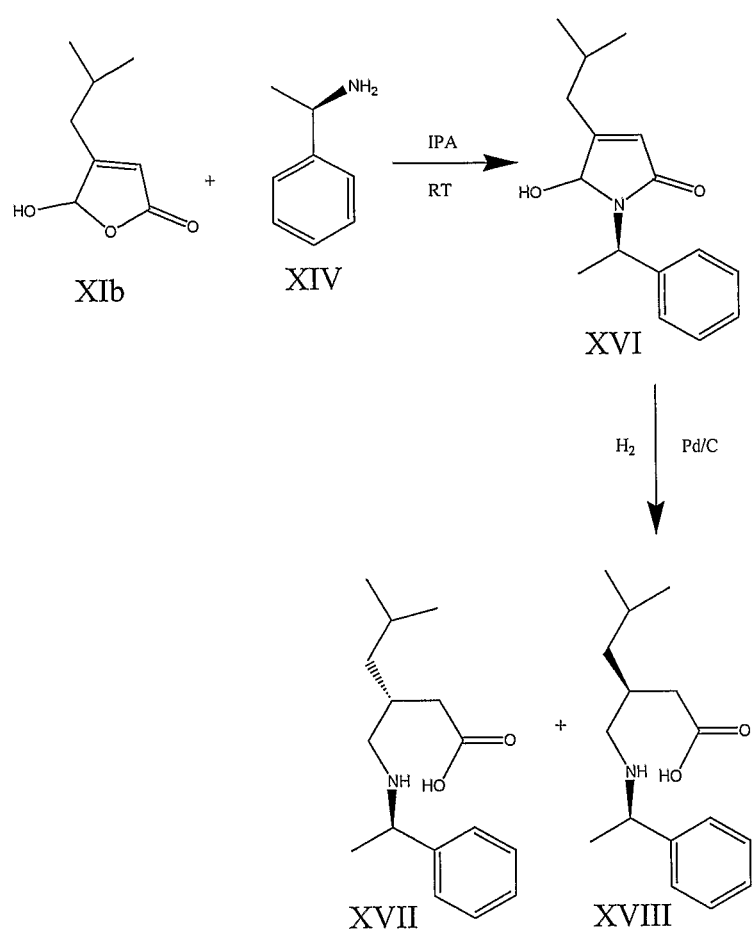

FIG. 9. Schematic representation of synthesis of compound [XVII] and [XVIII]

Figure 10:
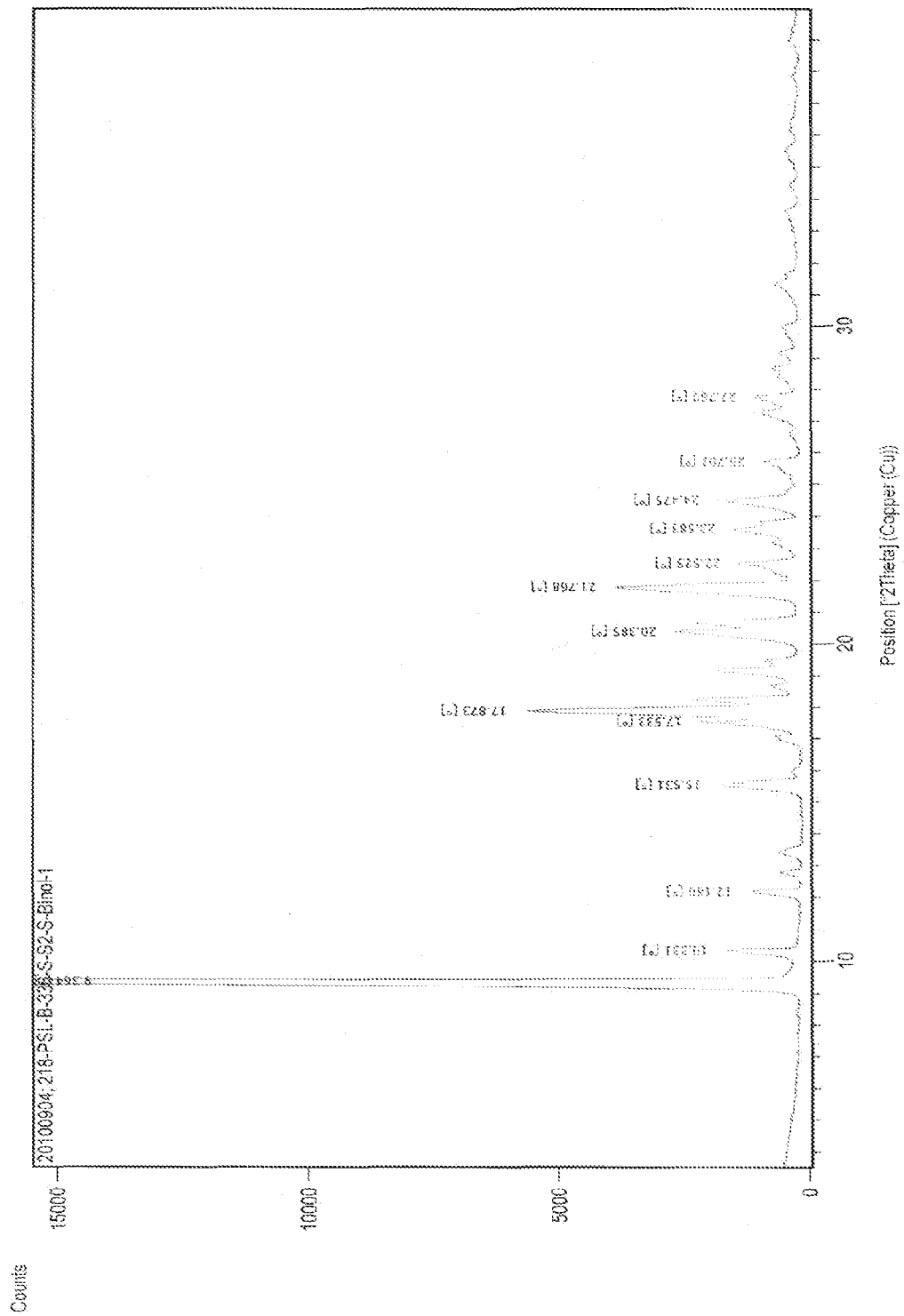

FIG. 10: PXRD of co-crystal of (S,S)-3-[(1-phenyl ethylamino)-methyl]-hexanoic acid: (8)-1,1'-bi-2-naphthol [VI]

Figure 11:
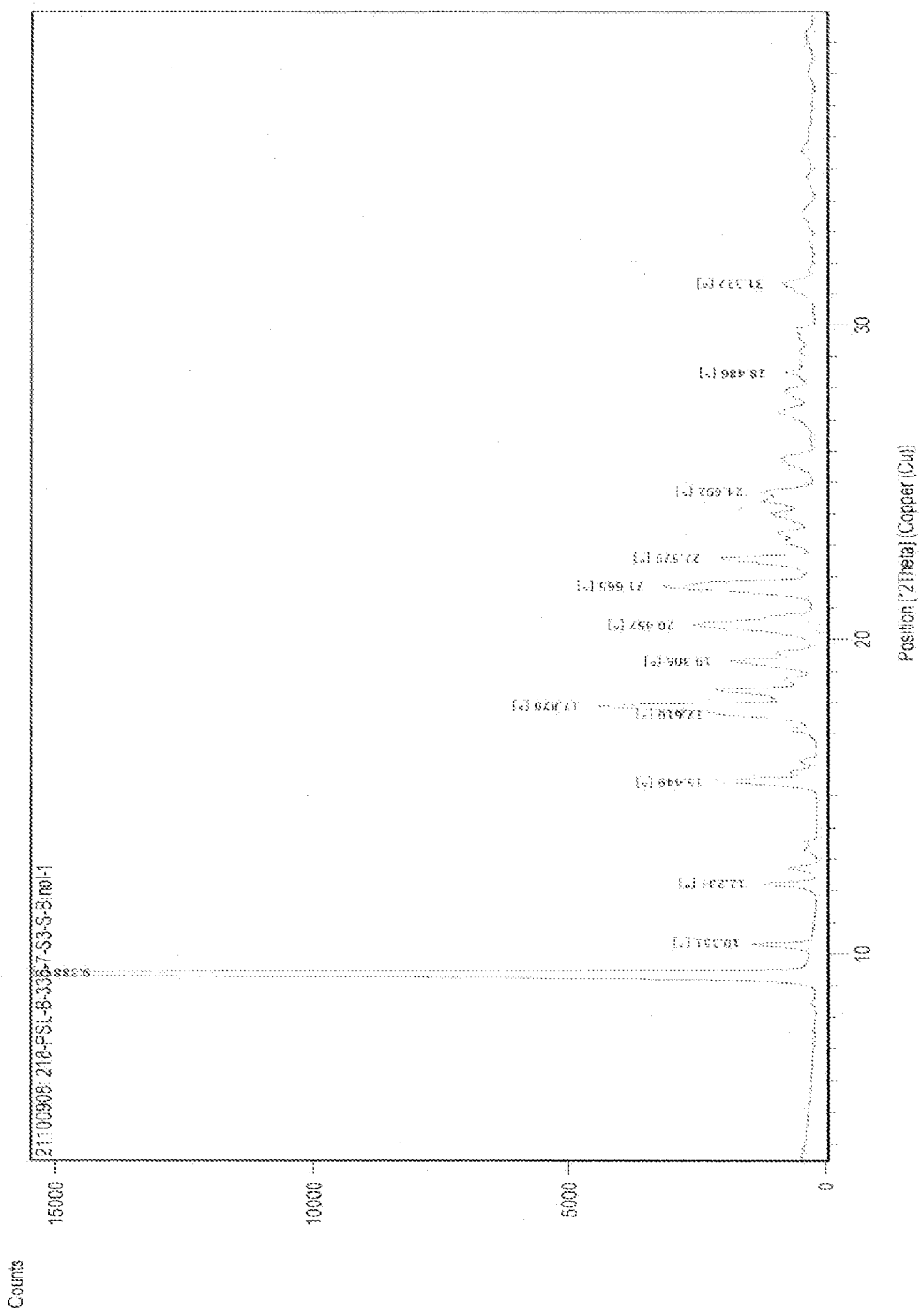

FIG. 11: PXRD of co-crystal of (R,S)-3-[(1-phenyl ethylamino)-methyl]-hexanoic acid: (S)-1,1'-bi-2-naphthol [VIII]

Figure 12:
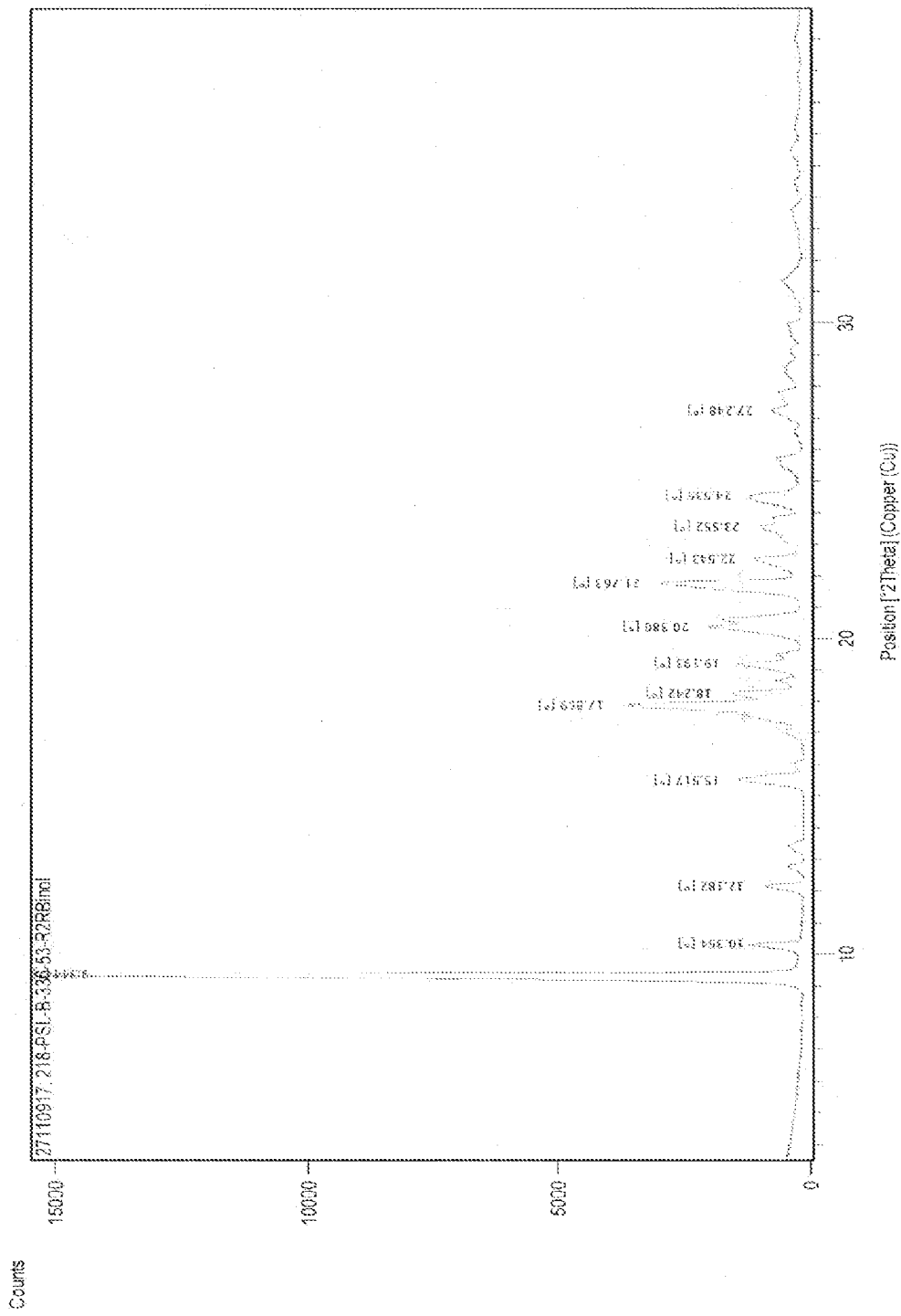

FIG. 12: PXRD of co-crystal of (R,R)-3-[(1-phenyl ethylamino)-methyl]-hexanoic acid: (R)-1,1'-bi-2-naphthol [V]

Figure 13:
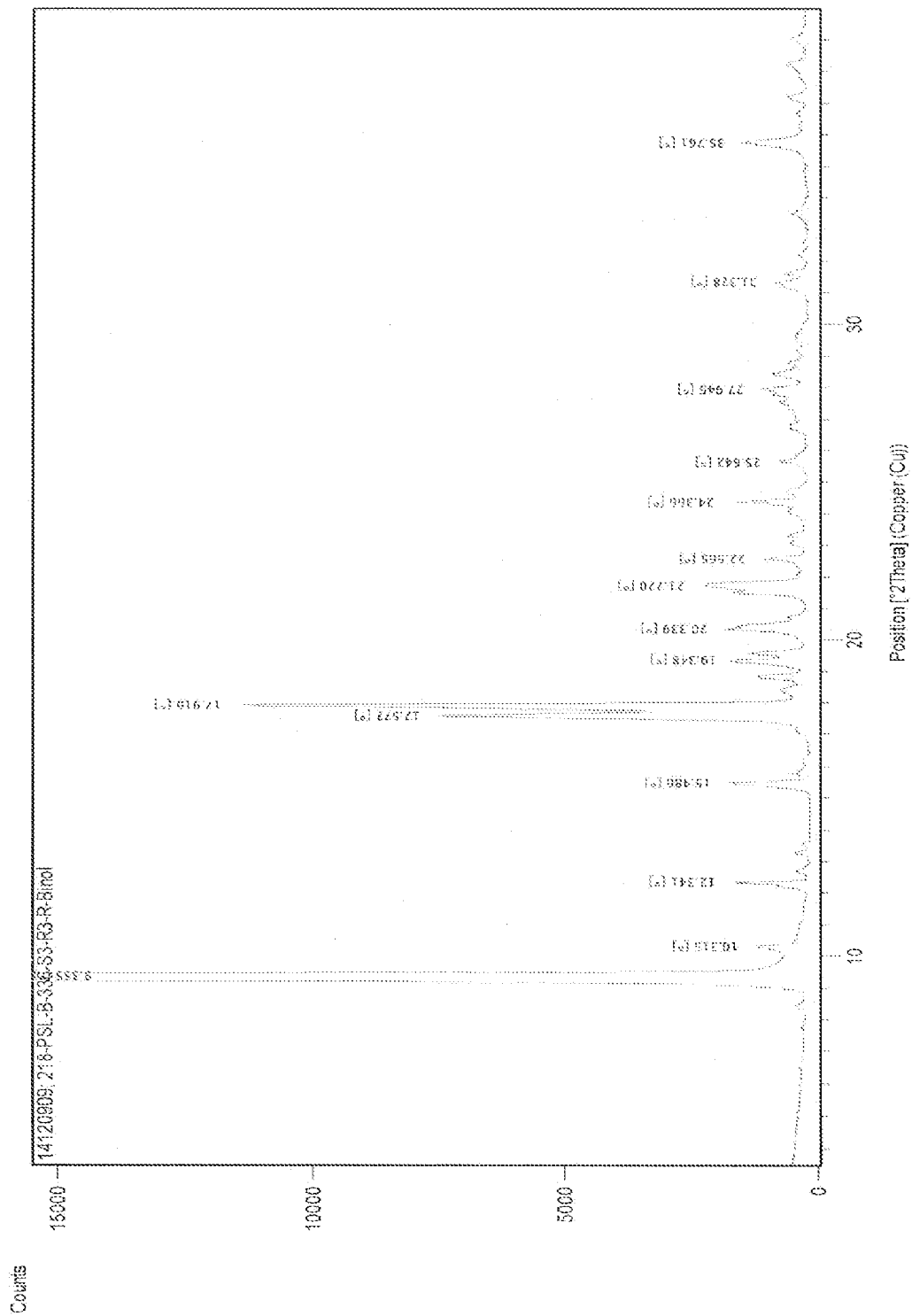

FIG. 13: PXRD of co-crystal of (S,R)-3-[(1-phenyl ethylamino)-methyl]-hexanoic acid: (R)-1,1'-bi-2-naphthol [IX]

Figure 14:
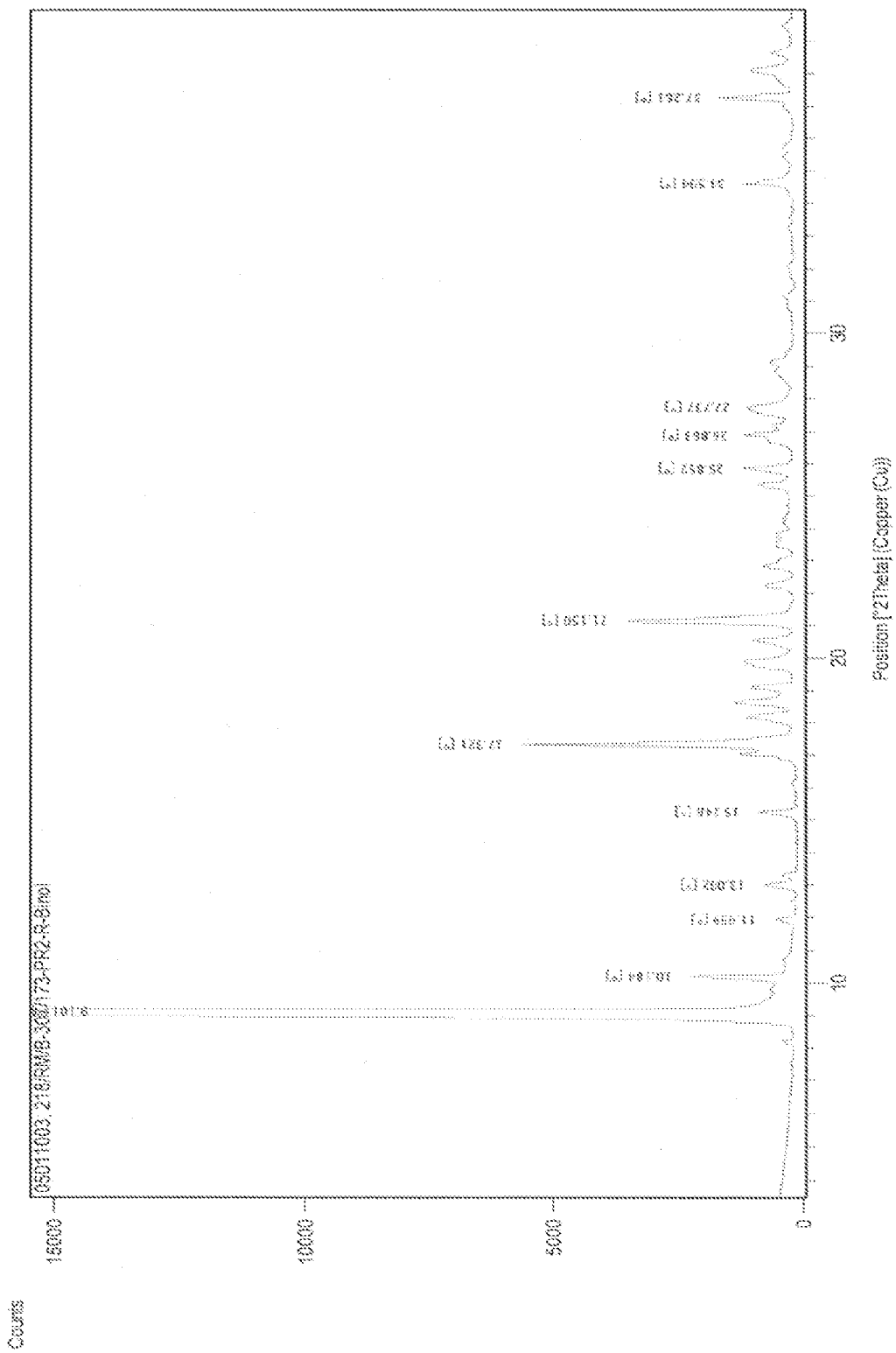
Figure 15:
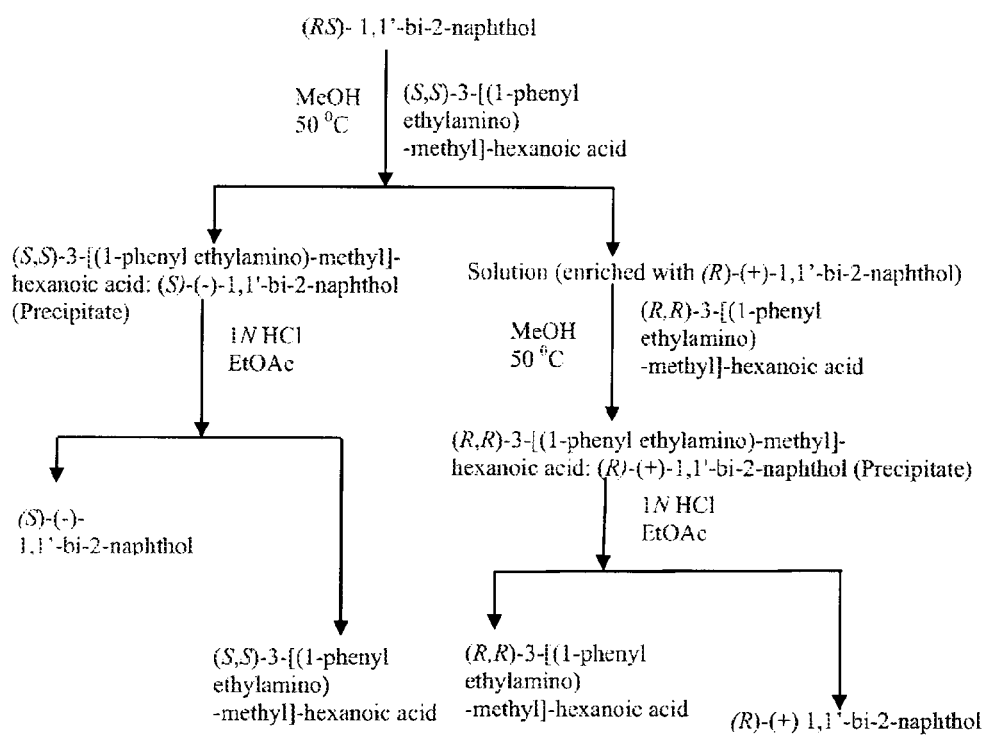
Figure 16:
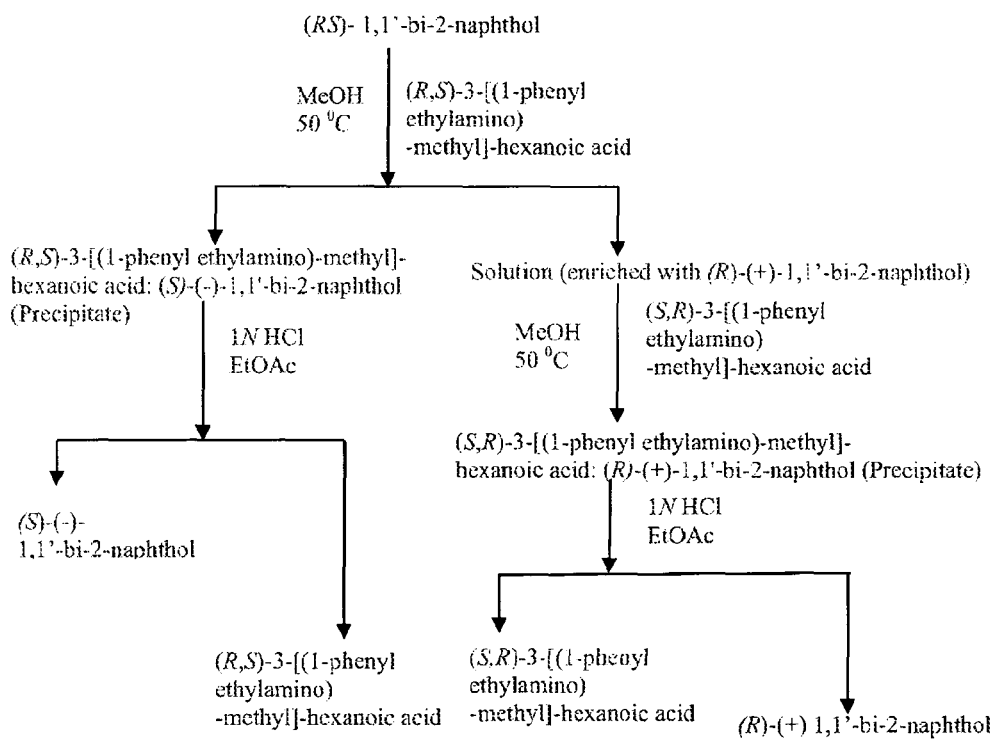

FIG. 14: PXRD of co-crystal of 5-methyl-3-[((R)-1-phenyl-ethylamino)-methyl]-hexanoic acid: (R)-1,1'-bi-2-naphthol FIG. 15. Schematic representation of the resolution of (RS)-1,1'-bi-2-naphthol to obtain (S)-1,1'-bi-2-naphthol and (R)-1,1'-bi-naphthol via co-crystal formation by sequential addition of co-crystal former i.e. (S,S)-3-[(1-phenyl ethylamino)-methyl]-hexanoic acid and (R,R)-3-[(1-phenyl ethylamino)-methyl]-hexanoic acid;

FIG. 16. Schematic representation of the resolution of (RS)-1,1'-bi-2-naphthol to obtain (S)-1,1'-bi-2-naphthol and (R)-1,1'-bi-2-naphthol via co-crystal formation by sequential addition of co-crystal former i.e. (R,S)-3-[(1-phenyl ethylamino)-methyl]-hexanoic acid and (S,R)-3-[(1-phenyl ethylamino)-methyl]-hexanoic acid as attached herein.

DETAILED DESCRIPTION

The invention embodies method for obtaining optically pure enantiomers of compound [I], having optical purity of >99% with high yield.

According to one embodiment of the invention, chiral separation of compound [I] to corresponding optically pure enantiomer is obtained via formation of co-crystal with substituted γ-amino acids.

According to one embodiment of the invention, co-crystal composition is 1:1 for which, the single crystal analysis details are given hereinafter.

Crystal structure of the single crystal of co-crystal [IV] is measured on Bruker Smart Apex CCD diffractometer having software SHELXTL-PLUS at temperature 293 (2) K and wavelength 0.71073 Å and θ range for data collection is 1.56 to 28.40°. Table 1 summarizes the crystal data and structure refinement and ORTEP diagram of the single crystal of co-crystal [IV] is given in FIG. 5.

TABLE 1

Crystal data and structure refinement of [II] and (S)-(−)-1,1'-bi-2-naphthol: co-crystal [IV]

| | |
|---|---|
| Empirical formula | $C_{35} H_{37} N O_4$ |
| Formula weight | 535.66 |
| Temperature | 293(2) K |
| Wavelength | 0.71073 Å |
| Crystal system | Orthorhombic |
| Space group | P212121 |
| Unit cell dimensions | a = 10.1158(18) Å   alpha = 90 deg. |
| | b = 11.293(2) Å    beta = 90 deg. |
| | c = 26.118(5) Å    gamma = 90 deg |
| Volume | 2983.8(9) Å$^3$ |
| Z | 4 |
| Density (calculated) | 1.192 g/cm$^3$ |
| Absorption coefficient | 0.077 mm$^{-1}$ |
| F(000) | 1144 |
| Crystal size | 0.44 × 0.40 × 0.28 mm |
| Theta range for data collection | 1.56 to 28.40 deg. |
| Index ranges | −10 <= h <= 12, −15 <= k <= 14, −33 <= l <= 34 |
| Reflections collected | 17943 |
| Independent reflections | 6929 [R(int) = 0.0313] |
| Absorption correction | Semi-empirical from equivalents |
| Max. and min. transmission | 0.9787 and 0.9669 |
| Refinement method | Full-matrix least-squares on F$^2$ |
| Data/restraints/parameters | 6929/0/365 |
| Goodness-of-fit on F$^2$ | 1.113 |
| Final R indices [I > 2sigma(I)] | $R_1$ = 0.0702, w$R_2$ = 0.1513 |
| R indices (all data) | $R_1$ = 0.0896, w$R_2$ = 0.1612 |
| Absolute structure parameter | −0.4(15) |
| Largest diff. peak and hole | 0.368 and −0.171 e · A$^{-3}$ |

Flack parameter factor is normally used to estimate the absolute configuration of a structure in single crystal structure analysis. To assign the correct absolute configuration, the Flack parameter value should be near to zero with small standard deviation and to achieve that requires a heavy atom to be attached to the compound. In the said γ-amino acid [II], there is no such heavy atom hence Flack parameter can not be used to assign the configuration. Hence by applying Cahn-Ingold-Prelog priority rule, the absolute configuration is defined. Stereochemistry of carbon atom 1 in [X] is "S" and it comes from (S)-α-methyl benzyl amine and on this basis, stereochemistry of carbon at 2 is assigned as "S".

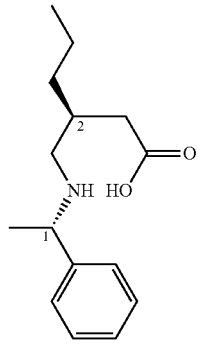

(X)

$^1$H NMR data and FTIR of γ-amino acid confirm the above structure, i.e. Carbon atom 1 and 2 of (VII) are both in 'S' configuration.

FTIR (KBr pellets): 2960, 1623, 1547 cm$^{-1}$;

$^1$H NMR (CDCl$_3$, 200 MHz): δ 0.84-0.86 (t, 3H), 1.13-1.18 (q, 2H), 1.21-1.26 (q, 2H), 1.69-1.70 (d, 3H), 2.14-2.18 (d, 2H), 2.51-2.58 (t, 2H), 2.75-2.78 (d, 1H), 4.12-4.17 (q, 1H), 7.35-7.42 (m, 3H), 7.47-7.51 (m, 2H);

MS (EI): C$_{15}$H$_{23}$NO$_2$: 249.17; [M+H]$^+$: 250.20

The sodium salt of compounds [II], [III], [VI] and [VII] show an IR band at 1730 cm$^{-1}$, indicating the presence of the free carboxylic acid. FTIR spectra of [II], [III], [VI] and [VII] show zwitterion patterns.

Powder X-ray diffraction data generated from single crystal of co-crystal (S,S)-3-[(1-phenyl ethylamino)-methyl]-hexanoic acid:(S)-(−)-1,1'-bi-2-naphthol is same as powder X-ray diffraction data obtained from bulk material.

Crystal structure of the single crystal of the co-crystal [VIII] is measured on Bruker Smart Apex CCD diffractometer having software SHELXTL-PLUS at temperature 293 (2) K and wavelength 0.71073 Å and θ range for data collection is 1.56 to 28.40°. Table 2 summarizes the crystal data and structure refinement and ORTEP diagram of the single crystal of co-crystal [VIII] is given in FIG. 6.

TABLE 2

Crystal data and structure refinement of [VI] and (S)-(−)-1,1'-bi-2-naphthol: co-crystal [VIII]

| | |
|---|---|
| Empirical formula | C$_{35}$H$_{37}$NO$_4$ |
| Formula weight | 535.66 |
| Temperature | 293(2) K |
| Wavelength | 0.71073 Å |
| Crystal system | Orthorhombic |
| Space group | P2$_1$2$_1$2$_1$ |
| Unit cell dimensions | a = 10.039 Å    alpha = 90 deg. |
| | b = 11.18 Å    beta = 90 deg. |
| | c = 26.35 Å    gamma = 90 deg |
| Volume | 2958.132 Å$^3$ |
| Z | 4 |
| Density (calculated) | 1.2 g/cm$^3$ |
| Absorption coefficient | 0.077 mm$^{-1}$ |
| F(000) | 1144 |
| Crystal size | 0.44 × 0.40 × 0.28 mm |
| Theta range for data collection | 1.56 to 26.290 deg. |
| R indices (all data) | R$_1$ = 0.0648, wR$_2$ = 0.1944 |

The said optically pure γ-amino acids are prepared by the procedure disclosed in our co-pending patent application entitle "Novel method for preparation of enantiomerically enriched and/or racemic γ-amino acids" and described hereinafter.

5-hydroxy-4-n-propyl-5H-furan-2-one [XIa] when reacted with (S)-(α)-methyl benzyl amine [XII] gives the compound [XIII]. Hydrogenation of compound [XIII] in isopropanol gives the diastereomeric compounds [II] and [VI], which get separated during the reaction. Compound [II] precipitates out from reaction, leaving compound [VI] dissolved in the reaction media. FIG. 7. gives the schematic representation.

5-hydroxy-4-n-propyl-5H-furan-2-one [XIa] when reacted with (R)-(α)-methyl benzyl amine [XIV] gives the compound [XV]. Hydrogenation of compound [XIII] in isopropanol gives the diastereomeric compounds [III] and [VII], which are separated during the reaction. Compound [III] precipitates out from reaction leaving compound [VII] dissolved in the reaction media. FIG. 8. gives the schematic representation.

5-hydroxy-4-iso-butyl-5H-furan-2-one [XIb] when reacted with (R)-(a)-methyl benzyl amine [XIV] gives the compound [XVI]. Hydrogenation of compound [XVI] in isopropanol gives mixture of diastereomeric compounds [XVII] and [XVIII]. FIG. 9 gives the schematic representation.

Physical properties of compounds [II], [III], [VI] and [VII] are summarized in Table 3

TABLE 3

Physical Properties of compounds [II], [III], [VI] and [VII]

| | Properties | | |
|---|---|---|---|
| Compound | Differential scanning calorimetry (10° C./min) Peak at ° C. | Specific optical rotation (c = 1% in methanol) at 25° C. | Powder X-ray diffraction pattern PXRD [2θ] (Cu K$_{α1}$ = 1.54060 Å, K$_{α2}$ = 1.54443 Å, K$_β$ = 1.39225 Å; 40 mA, 45 kV) |
| (S,S)-3-[(1-phenyl ethylamino)-methyl]-hexanoic acid [II] | 147.16 | (−) 3.4 | 7.66, 10.44, 15.09, 16.55, 19.52, 22.33, 26.93, 33.74 |
| (R,R)-3-[(1-phenyl ethylamino)-methyl]-hexanoic acid [III] | 148.11 | (+) 3.6 | 7.67, 10.45, 15.10, 16.55, 19.47, 22.33, 26.92, 33.78 |

TABLE 3-continued

Physical Properties of compounds [II], [III], [VI] and [VII]

| Compound | Properties | | |
|---|---|---|---|
| | Differential scanning calorimetry (10° C./min) Peak at ° C. | Specific optical rotation (c = 1% in methanol) at 25° C. | Powder X-ray diffraction pattern PXRD [2θ] (Cu $K_{\alpha 1}$ = 1.54060 Å, $K_{\alpha 2}$ = 1.54443 Å, $K_{\beta}$ = 1.39225 Å; 40 mA, 45 kV) |
| (R,S)-3-[(1-phenyl ethylamino)-methyl]-hexanoic acid [VI] | 120.10 | (−) 11.3 | 6.61, 7.54, 11.47, 14.94, 17.04, 17.62, 19.57, 22.24, 22.68, 26.24 |
| (S,R)-3-[(1-phenyl ethylamino)-methyl]-hexanoic acid [VII] | 119.3 | (+) 11.5 | 6.62, 7.52, 11.48, 14.97, 17.09, 17.60, 19.69, 22.23, 22.72, 26.26 |

Compound [II] with (S)-1,1'-bi-naphthol gives the co-crystal (S,S)-3-[(1-phenyl ethylamino)-methyl]-hexanoic acid: (S)-(−)-1,1'-bi-2-naphthol [IV] and compound [VI] with (S)-(−)-1,1'-bi-2-naphthol gives (R,S)-3-[(1-phenylethylamino)-methyl]-hexanoic acid: (S)-(−)-1,1'-bi-2-naphthol [VIII].

Compound [III] with (R)-1,1'-bi-naphthol gives the co-crystal (R,R)-3-[(1-phenyl ethylamino)-methyl]-hexanoic acid: (R)-(+)-1,1'-bi-2-naphthol [V] and compound [VII] with (R)-(+)-1,1'-bi-naphthol gives the co-crystal (S,R)-3-[(1-phenylethylamino)-methyl]-hexanoic acid: (R)-(+)-1,1'-bi-2-naphthol [IX].

Physical properties of co-crystals [IV], [V] [VIII] and [IX] are summarized in Table 4.

TABLE 4

Physical properties of co-crystals [IV], [V] [VIII] and [IX]

| Co-crystal | Properties | | | |
|---|---|---|---|---|
| | Differential scanning calorimetry (10° C./min) Peak at ° C. | Specific optical rotation (c = 1 in methanol) at 25° C. | Powder x-ray diffraction pattern PXRD [2θ] (Cu $K_{\alpha 1}$ = 1.54060 Å, $K_{\alpha 2}$ = 1.54443 Å, $K_{\beta}$ = 1.39225 Å; 40 mA, 45 kV) | FTIR Spectral Data $(cm^{-1})$ |
| (S,S)-3-[(1-phenyl ethylamino)-methyl]-hexanoic acid: (S)-(−)-1,1'-bi-2-naphthol [IV] | 185.82 | (−) 15.71 | 9.36, 10.33, 12.17, 15.53, 17.53, 17.87, 17.96, 20,38, 21.76, 22.52, 24.47 and 27.76; | 3449, 3059, 2960, 2458, 1620, 1595, 1557, 1504, 1458, 1431, 1397, 1324, 1307, 1275, 1139, 1123, 818, 750, 709 |
| (R,R)-3-[(1-phenyl ethylamino)-methyl]-hexanoic acid: (R)-(+)-1,1'-bi-2-naphthol [V] | 186.71 | (+) 16.44 | 9.34, 10.35, 12.18, 15.51, 15.66, 17.04, 17.55, 17.86, 18.24, 18.67, 19.19, 20.37, 20.62, 21.54, 21.76, 22.54, 23.55, 24.53 and 27.24 | 3449, 3059, 2960, 2458, 1620, 1595, 1557, 1504, 1458, 1431, 1397, 1324, 1307, 1275, 1139, 1123, 818, 750, 709 |
| (R,S)-3-[(1-phenyl ethylamino)-methyl]-hexanoic acid: (S)-(−)-1,1'-bi-2-naphthol [VIII] | 177.69 | (−) 18.46 | 9.38, 10.35, 12.23, 15.44, 15.51, 17.60, 17.87, 19.30, 20.45, 21.66, 22.57, 24.41, 24.69 and 28.48 | 3449, 3059, 2960, 2458, 1620, 1595, 1557, 1504, 1458, 1431, 1397, 1324, 1307, 1275, 1139, 1123, 818, 750, 709 |
| (S,R)-3-[(1-phenyl ethylamino)-methyl]-hexanoic acid: (R)-(+)-1,1'-bi-2-naphthol [IX] | 172.62 | (+) 19.97 | 9.25, 10.31, 12.23, 15.44, 15.51, 17.60, 17.87, 19.30, 20.45, 21.66, 22.57, 24.41, 24.69 and 28.48 | 3449, 3059, 2960, 2458, 1620, 1595, 1557, 1504, 1458, 1431, 1397, 1324, 1307, 1275, 1139, 1123, 818, 750, 709 |

Table 5 gives the comparative data of FTIR spectra of free racemic (RS)-1,1'-bi-2-naphthol [I], co-crystal [(S,S)-3-[(1-phenyl ethylamino)-methyl]-hexanoic acid:(S)-(−)-1,1'-bi-2-naphthol] [IV] and (S,S)-3-[(1-phenyl ethylamino)-methyl]-hexanoic acid [II].

TABLE 5

FTIR spectral data of Compound [I], [II] and [IV]

| Co-crystal of (S,S)-3-[(1-phenyl ethylamino)-methyl]-hexanoic acid & (S)-(−)-1,1'-bi-2-naphthol [IV] * ($cm^{-1}$) | (RS)-1,1'-bi-2-naphthol [I] * ($cm^{-1}$) | (S,S)-3-[(1-phenyl ethylamino)-methyl]-hexanoic acid [II] * ($cm^{-1}$) |
|---|---|---|
| 3449, 3059, 2960, 2458, 1620, 1595, 1557, 1504, 1458, 1431, 1397, 1324, 1307, 1275, 1139, 1123, 818, 750, 709 | 3486, 3402, 1617, 1596, 1510, 1461, 1470, 1381, 1217, 1174, 1146, 826, 751, 573 | 3444, 2960, 1623, 1547, 1497, 1397, 703 |

* FTIR absorption peak observed by preparing pellet of solid of respective compound dispersed in dry potassium bromide.

Surprisingly it is observed that compound [III] and compound [VII] are diastereomers, where the stereo-configuration at benzylic center is same i.e. "R". When these compounds are reacted with (R)-(+)-1,1'-bi-naphthol, they give the co-crystals [V] and [IX] respectively. Similarly it is also observed that compound [II] and [VI] are diastereomers, where the stereo-configuration at benzylic center is same i.e. "S". When these compounds are reacted with (S)-(−)-1,1'-bi-naphthol, they give the co-crystals [IV] and [VIII] respectively.

Hence, it can be hypothesized that irrespective of stereo-configuration at alkyl chain, stereo-configuration at benzylic center is the deciding factor for stereo specific co-crystal formation. This postulation have been found true for 5-methyl-3-[((R)-1-phenyl-ethylamino)-methyl]-hexanoic acid i.e. the diastereomeric mixture of compounds [XVII] and [XVIII]. When the mixture is treated with (R)-(+)-1,1'-bi-naphthol it gives the co-crystal 5-methyl-3-[((R)-1-phenyl-ethylamino)-methyl]-hexanoic acid: (R)-(+)-1,1'-bi-naphthol, which precipitates out from the reaction media and similarly when diastereomeric mixture of compounds [XVII] and [XVIII] is treated with (S)-(−)-1,1'-bi-naphthol it remains dissolved in reaction media. Hence it could be a method for resolution of (RS)-1,1'-bi-naphthol to obtain optically pure (S) or (R)-1,1'-bi-naphthol.

Powder x-ray diffraction pattern for co-crystal 5-methyl-3-[((R)-1-phenyl-ethylamino)-methyl]-hexanoic acid (diastereomeric mixture of compound [XVII] and [XVIII]): (R)-(+)-1,1'-bi-naphthol is given in FIG. 14.

In all cases, the co-crystal formation of the optically active γ-amino acids with compound [I] is carried out in an alcoholic solvent, preferably methanol.

In all cases, the co-crystal formation of compound [I] with optically active γ-amino acids is carried out at a temperature range of 25-60° C., preferably at 50° C.

Molar ratio of optically pure γ-amino acids to compound [I] varies from 0.5 to 1.5 mol equivalents, preferably 0.5 mol equivalent is used.

The co-crystals of compound [I] with optically active γ-amino acids are decomposed in a biphasic mixture of ethyl acetate: dilute hydrochloric acid (1:1) at room temperature.

The optically active γ-amino acids are recovered from the aqueous phase by neutralizing the aqueous dilute hydrochloric acid with dilute sodium bicarbonate solution and are reused.

Nomenclatures used for the compounds mentioned herein are as understood from the CambridgeSoft® ChemOffice software ChemDraw Ultra version 6.0.1.

Analytical Methods:

The enantiomeric excess (ee) is determined by HPLC using a Shimadzu LC 2010 system equipped with a chiral column (Chiral pak IA, 4.6 mm×250 mm, 5 μm), column oven temperature 40° C. and UV visible detector (230 nm). Mobile phase is n-hexane (94):n-butanol (5): ethanol (1): Trifluoacetic acid (0.3 mL) with flow rate 1 $mL^{-1}$, injection volume 20 μl. NMR spectra are obtained at 200 and 400 MHz Bruker instruments, with $CDCl_3$ as solvent. Chemical shifts (δ) are given in ppm relative to tetramethylsilane (δ=0 ppm). IR spectra are recorded on Perkin Elmer Spectrum (Model: Spectrum 100) and absorption bands are given in $cm^{-1}$. DSC is recorded on Perkin Elmer model Diamond DSC at the rate of 10° C./min, and endothermic peak is recorded in ° C. and ΔH is reported in J/g.

Example 1

Synthesis of 5-hydroxy-4-n-propyl-5H-furan-2-one [XI](Reference: J. Org. Chem. 1981, 46, 4889-4894)

Heptane (394 mL) and morpholine (127.5 mL) are introduced in a reactor while stirring. The mixture is cooled to 0° C. and glyoxylic acid (195 g, 150 mL, 50 wt % in water) is added. The mixture is heated to 20° C. during 1 hour and then n-valeraldehyde (148.8 mL) is added. The reaction mixture is heated at 45° C. during 20 hours. After cooling down to 20° C., a 37% aqueous solution of hydrochloric acid (196.9 mL) is slowly added to the mixture, which is then stirred during 2 hours.

After removal of the heptane phase, the aqueous phase is washed three times with heptane. Di-iso-propyl ether is added to the aqueous phase. The organic phase is removed and the aqueous phase further extracted with di-iso-propyl ether (2×). The diisopropyl ether layers are combined, washed with brine and then dried under reduced pressure. After evaporation of the solvent, 100.0 g of 5-hydroxy-4-n-propyl-5H-furan-2-one are obtained as light brown oil.

FTIR (neat): 3367, 1735 $cm^{-1}$.

$^1$H NMR ($CDCl_3$, 200 MHz): δ 0.93-1.00 (t, 3H), 1.56-1.67 (q, 2H), 2.31-2.43 (q, 2H), 5.81 (s, 1H), 6.02 (s, 1H).

MS (EI): $C_7H_{10}O_3$: 142.06; $[M+H]^+$: 142.93.

Example 2

Synthesis of 5-hydroxy-1-[(S)-phenyl-ethyl]-4-n-propyl-1,5-dihydro-pyrrol-2-one [XIII]

5-hydroxy-4-n-propyl-5H-furan-2-one (10.0 g) is dissolved in iso-propanol (100 mL) and (5)-α-methyl benzyl amine (8.5 g) is added to it at room temperature. The mixture is stirred at room temperature for 1 hour. After completion of the reaction (monitored by TLC, 1:1 ethyl acetate:hexane), the solvent is evaporated under reduced pressure in a rotary evaporator to afford 5-hydroxy-1-[(S)-phenyl-ethyl]-4-n-propyl-1,5-dihydro-pyrrol-2-one as dark yellow oil (16.5 g).

FTIR (neat): 3321, 1749, 1165 $cm^{-1}$.

$^1$H NMR ($CDCl_3$, 200 MHz): δ 0.86-0.94 (t, 3H), 1.31-1.37 (t, 3H), 1.43-1.57 (m, 2H), 2.12-2.39 (m, 2H), 4.27-4.30 (d, 1H), 5.15 (s, 1H), 5.70 (s, 1H), 7.25-7.34 (m, 5H).

MS (EI): $C_{15}H_{19}NO_2$: 245.14; $[M+H]^+$: 246.51.

Example 3

Synthesis of 5-hydroxy-1-[(R)-phenyl-ethyl]-4-n-propyl-1,5-dihydro-pyrrol-2-one [XV]

5-hydroxy-4-n-propyl-5H-furan-2-one (10.0 g) is dissolved in iso-propanol (100 mL) and (R)-α-methyl benzyl amine (8.5 g) is added to it at room temperature. The mixture is stirred at room temperature for 1 hour. After completion of the reaction (monitored by TLC, 1:1 ethyl acetate:hexane), the solvent is evaporated under reduced pressure in a rotary evaporator to afford 5-hydroxy-1-[(R)-phenyl-ethyl]-4-n-propyl-1,5-dihydro-pyrrol-2-one as dark yellow oil (16.5 g).

FTIR (neat): 3321, 1749, 1165 $cm^{-1}$.

$^1$H NMR ($CDCl_3$, 200 MHz): δ 0.86-0.94 (t, 3H), 1.31-1.37 (t, 3H), 1.43-1.57 (m, 2H), 2.12-2.39 (m, 2H), 4.27-4.30 (d, 1H), 5.15 (s, 1H), 5.70 (s, 1H), 7.25-7.34 (m, 5H).

MS (EI): $C_{15}H_{19}NO_2$: 245.14; $[M+H]^+$: 246.51.

Example 4

Hydrogenation of 5-hydroxy-1-[(S)-phenyl-ethyl]-4-n-propyl-1,5-dihydro-pyrrol-2-one [XIII] with Pd/C 5-hydroxy-1-[(S)-phenyl-ethyl]-4-n-propyl-1,5-dihydro-pyrrol-2-one (16.5 g) is dissolved in iso-propanol (100 mL) in a Parr autoclave reactor followed by addition of 50% wet palladium-on-carbon (Pd/C) at 10% catalyst loading. Reactor is purged with hydrogen gas twice and then 3 kg/$cm^2$ hydrogen pressure is maintained. Reaction is monitored by TLC [chloroform:methanol (9:1)]. After complete consumption of starting material, the reaction is stopped. In the reaction, diastereomers separate; (S,S)-3-[(1-phenyl ethylamino)-methyl]-hexanoic acid precipitates out from the reaction media and (R,S)-3-[(1-phenyl ethylamino)-methyl]-hexanoic acid remains dissolved in the reaction media.

After completion of reaction, the reaction mixture is filtered and filtrate is concentrated under vacuum to obtain a semi solid material, which is suspended in cyclohexane (300 mL) and stirred overnight to yield 6.5 g of (R,S)-3-[(1-phenyl ethylamino)-methyl]-hexanoic acid as a off-white solid obtained after vacuum filtration.

Filtered cake contains Pd/C and (S,S)-3-[(1-phenyl ethylamino)-methyl]-hexanoic acid which is suspended in 50 ml methanol and stirred for 20 min to dissolve (S,S)-3-[(1-phenyl ethylamino)-methyl]-hexanoic acid. Pd/C is separated by filtration. Filtrate is concentrated under vacuum to obtain 8.0 g of (S,S)-3-[(1-phenyl ethylamino)-methyl]-hexanoic acid as a white solid.

(S,S)-3-[(1-phenyl ethylamino)-methyl]-hexanoic acid [II]

FTIR (KBr pellets): 2960, 1623, 1547 $cm^{-1}$;

$^1$H NMR ($CDCl_3$, 200 MHz): δ 0.84-0.86 (t, 3H), 1.13-1.18 (q, 2H), 1.21-1.26 (q, 2H), 1.69-1.70 (d, 3H), 2.14-2.18 (d, 2H), 2.51-2.58 (t, 2H), 2.75-2.78 (d, 1H), 4.12-4.17 (q, 1H), 7.35-7.42 (m, 3H), 7.47-7.51 (m, 2H); MS (EI): $C_{15}H_{23}NO_2$: 249.17; $[M+H]^+$: 250.20

DSC (10° C./min): Peak at 147.16° C.

(R,S)-3-[(1-phenyl ethylamino)-methyl]-hexanoic acid [VI]

FTIR (KBr pellets): 2956, 1619, 1549, 1400 $cm^{-1}$;

$^1$H NMR ($CDCl_3$, 200 MHz): δ 0.76-0.79 (t, 3H), 1.14-1.23 (m, 4H), 1.66-1.68 (d, 3H), 2.26-2.30 (m, 2H), 2.53-2.59 (t, 2H), 2.77-2.80 (d, 1H), 4.06-4.11 (q, 1H), 7.31-7.57 (m, 5H);

MS (EI): $C_{15}H_{23}NO_2$: 249.17; $[M+H]^+$: 250.05.

DSC (10° C./min): Peak at 120.1° C.

Example 5

Hydrogenation of 5-hydroxy-1-[(R)-phenyl-ethyl]-4-n-propyl-1,5-dihydro-pyrrol-2-one [IX] with Pd/C 5-hydroxy-1-[(R)-phenyl-ethyl]-4-n-propyl-1,5-dihydro-pyrrol-2-one (16.5 g) is dissolved in iso-propanol (100 mL) in a Parr autoclave reactor followed by addition of 50% wet palladium-on-carbon (Pd/C) at 10% catalyst loading. Reactor is purged with hydrogen gas twice and then 3 kg/$cm^2$ hydrogen pressure is maintained. Reaction is monitored by TLC [chloroform:methanol (9:1)]. After complete consumption of starting material, the reaction is stopped. In the reaction, diastereomers separate; (R,R)-3-[(1-phenyl ethylamino)-methyl]-hexanoic acid precipitates out from the reaction media and (S,R)-3-[(1-phenyl ethylamino)-methyl]-hexanoic acid remains dissolved in the reaction media.

After completion of reaction, the reaction mixture is filtered and filtrate is concentrated under vacuum to obtain a semi solid material, which is suspended in cyclohexane (300 mL) and stirred overnight to yield 6.0 g of (S,R)-3-[(1-phenyl ethylamino)-methyl]-hexanoic acid as a off-white solid obtained after vacuum filtration.

Filtered cake, which contains Pd/C and (R,R)-3-[(1-phenyl ethylamino)-methyl]-hexanoic acid is suspended in 50 ml methanol and stirred for 20 min to dissolve (R,R)-3-[(1-phenyl ethylamino)-methyl]-hexanoic acid. Pd/C is separated by filtration. Filtrate is concentrated under vacuum to obtain 8.0 g of (R,R)-3-[(1-phenyl ethylamino)-methyl]-hexanoic acid as white solid.

(R,R)-3-[(1-phenyl ethylamino)-methyl]-hexanoic acid [III]

FTIR (KBr pellets): 2958, 1621, 1548, 1397 $cm^{-1}$.

$^1$H NMR ($CDCl_3$, 200 MHz): δ 0.80-0.87 (t, 3H), 1.17-1.22 (m, 4H), 1.67-1.70 (d, 3H), 2.13-2.19 (d, 2H), 2.44-2.61 (t, 2H), 2.74-2.80 (d, 1H), 4.11-4.20 (q, 1H), 7.30-7.54 (m, 5H).

MS (EI): $C_{15}H_{23}NO_2$: 249.17; $[M+H]^+$: 250.03.

DSC (10° C./min): Peak at 148.11° C.

(S,R)-3-[(1-phenyl ethylamino)-methyl]-hexanoic acid [VII]

FTIR (KBr pellets): 2957, 1620, 1550, 1399 $cm^{-1}$.

$^1$H NMR ($CDCl_3$, 200 MHz): δ 0.75-0.81 (t, 3H), 1.18-1.41 (m, 4H), 1.65-1.69 (d, 3H), 2.20-2.33 (m, 2H), 2.49-2.60 (t, 2H), 2.76-2.82 (d, 1H), 4.07-4.17 (q, 1H), 7.32-7.54 (m, 5H).

MS (EI): $C_{15}H_{23}NO_2$: 249.17; $[M+H]^+$: 250.50.

DSC (10° C./min): Peak at 119.3° C.

Example 6

Diastereomeric Co-Crystal Formation of (S,S)-3-[(1-phenyl ethylamino)-methyl]-hexanoic acid with (S)-1,1'-bi-2-naphthol (S,S)-3-[(1-phenyl ethylamino)-methyl]-hexanoic acid (1.0 g) is dissolved in methanol (20 mL) and (S)-1,1'-bi-2- naphthol (1.15 g) is added to it at room temperature. The solution is stirred at 50° C. for 1 hour; during which time solid precipitate comes out from the reaction mixture. Reaction mixture is allowed to cool to room temperature and filtered under reduced pressure to obtain 1.55 g of the complex. FIG. 10. PXRD of co-crystal of (S,S)-3-[(1-phenyl ethylamino)-methyl]-hexanoic acid: (S)-1,1'-bi-2-naphthol [VI]

DSC (10° C./min): Peak at 185.82° C.

Example 7

Diastereomeric Co-Crystal Formation of (S,S)-3-[(1-phenyl ethylamino)-methyl]-hexanoic acid with (R)-1,1'-bi-2-naphthol (S,S)-3-[(1-phenyl ethylamino)-methyl]-hexanoic acid (1.0 g) is dissolved in methanol (20 mL) and (R)-1,1'-bi-2-naphthol (1.15 g) is added to it at room temperature. The mixture is stirred at 50° C. for 1 hour. Reaction mixture is allowed to cool to room temperature and solvent is evaporated under vacuum to obtain solid (2.0 g); PXRD analysis of obtained solid shows that it is amorphous in nature.

Example 8

Diastereomeric Co-Crystal Formation of (R,S)-3-[(1-phenyl ethylamino)-methyl]-hexanoic acid with (S)-1,1'-bi-2-naphthol (R,S)-3-[(1-phenyl ethylamino)-methyl]-hexanoic acid (1.0 g) is dissolved in methanol (20 mL) and (S)-1,1'-bi-2-naphthol (1.15 g) is added to it at room temperature. The mixture is stirred at 50° C. for 1 hour, during which time solid precipitate comes out from the reaction mixture. Reaction mixture is allowed to cool to room temperature and filtered under reduced pressure to obtain 1.45 g of the complex. FIG. 11. PXRD of co-crystal (R,S)-3-[(1-phenyl ethylamino)-methyl]-hexanoic acid: (S)-1,1'-bi-2-naphthol [VIII].

DSC (10° C./min): Peak at 177.69° C.

Example 9

Diastereomeric Co-Crystal Formation of (R,S)-3-[(1-phenyl ethylamino)-methyl]-hexanoic acid with (R)-1,1'-bi-2-naphthol (R,S)-3-[(1-phenyl ethylamino)-methyl]-hexanoic acid (1.0 g) is dissolved in methanol (20 mL) and (R)-1,1'-bi-2-naphthol (1.15 g) is added to it at room temperature. The mixture is stirred at 50° C. for 1 hour. Reaction mixture is allowed to cool to room temperature and solvent evaporated under vacuum to obtain solid; PXRD analysis of obtained solid shows that it is amorphous in nature.

Example 10

Diastereomeric Co-Crystal Formation of (R,R)-3-[(1-phenyl ethylamino)-methyl]-hexanoic acid with (R)-1,1'-bi-2-naphthol (R,R)-3-[(1-phenyl ethylamino)-methyl]hexanoic acid (1.0 g) is dissolved in methanol (20 mL) and (R)-1,1'-bi-2-naphthol (1.15 g) is added to it at room temperature. The mixture is stirred at 50° C. for 1 hour, during which time solid precipitate comes out from the reaction mixture. Reaction mixture is allowed to cool to room temperature and filtered under reduced pressure to obtain 1.5 g of the complex. FIG. 12. PXRD of co-crystal (R,R)-3-[(1-phenyl ethylamino)-methyl]-hexanoic acid: (R)-1,1'-bi-2-naphthol [V].

DSC (10° C./min): Peak at 186.71° C.

Example 11

Diastereomeric Co-Crystal Formation of (R,R)-3-[(1-phenyl ethylamino)-methyl]-hexanoic acid with (S)-1,1'-bi-2-naphthol (R,R)-3-[(1-phenyl ethylamino)-methyl]-hexanoic acid (1.0 g) is dissolved in methanol (20 mL) and (5)-1,1'-bi-2-naphthol (1.15 g) is added to it at room temperature. The mixture is stirred at 50° C. for 1 hour. Reaction mixture is allowed to cool to room temperature and solvent evaporated under vacuum to obtain solid; PXRD analysis of obtained solid shows that it is amorphous in nature.

Example 12

Diastereomeric Co-Crystal Formation of (S,R)-3-[(1-phenyl ethylamino)-methyl]-hexanoic acid with (R)-1,1'-bi-2-naphthol (S,R)-3-[(1-phenyl ethylamino)-methyl]-hexanoic acid (1.0 g) is dissolved in methanol (20 mL) and (R)-1,1'-bi-2-naphthol (1.15 g) is added to it at room temperature. The mixture is stirred at 50° C. for 1 hour, during which time solid precipitate comes out from the reaction mixture. Reaction mixture was allowed to cool to room temperature and filtered under reduced pressure to obtain 1.6 g of the complex. FIG. 13. PXRD of co-crystal (S,R)-3-[(1-phenyl ethylamino)-methyl]-hexanoic acid: (R)-1,1'-bi-2-naphthol [IX].

DSC (10° C./min): Peak at 172.62° C.

Example 13

Diastereomeric Co-Crystal of (S,R)-3-[(1-phenyl ethylamino)-methyl]-hexanoic acid with (S)-1,1'-bi-2-naphthol (R,R)-3-[(1-phenyl ethylamino)-methyl]-hexanoic acid (1.0 g) is dissolved in methanol (20 mL) and (S)-1,1'-bi-2-naphthol (1.15 g) is added to it at room temperature. The mixture is stirred at 50° C. for 1 hour. Reaction mixture is allowed to cool to room temperature and solvent evaporated under vacuum to obtain solid; PXRD analysis of obtained solid shows that it is amorphous in nature.

Example 14

Separation of (S)-1,1'-bi-2-naphthol from (RS)-1,1'-bi-2-naphthol Via Formation of Diastereomeric Co-Crystal with (S,S)-3-[(1-phenyl ethylamino)-methyl]-hexanoic acid (S,S)-3-[(1-phenyl ethylamino)-methyl]-hexanoic acid (5.0 g) is dissolved in methanol (20 mL) and (RS)-1,1'-bi-2-naphthol (5.75 g) is added to it at room temperature. The mixture is stirred at 50° C. for 1 hour, during which time solid precipitate comes out from the reaction mixture. Reaction mixture is allowed to cool to room temperature and filtered under reduced pressure to obtain 3.5 g of solid complex. Complex is suspended in the biphasic mixture of ethyl acetate (20 ml) and 1N hydrochloric acid (20 ml) and stirred for 30 to 45 min to decompose the complex. Aqueous phase is washed with 10 mL ethyl acetate. Organic phases are mixed together and washed with brine, followed by drying over sodium sulfate. Solvent is evaporated under vacuum to obtain optically pure (S)-1,1'-bi-2-naphthol (1.5 g) having 99% ee.

The acid aqueous solution which contains hydrochloride salt of (S,S)-3-[(1-phenyl ethylamino)-methyl]-hexanoic acid is neutralized with dilute solution of sodium bicarbonate to recover the (S,S)-3-[(1-phenyl ethylamino)-methyl]-hexanoic acid (0.8 g).

Example 15

Separation of (S)-1,1'-bi-2-naphthol from (RS)-1,1'-bi-2-naphthol Via Formation of Diastereomeric Co-Crystal with (R,S)-3-[(1-phenyl ethylamino)-methyl]-hexanoic acid (R,S)-3-[(1-phenyl ethylamino)-methyl]-hexanoic acid (5.0 g) is dissolved in methanol (20 mL) and (RS)-1,1'-bi-2-naphthol (5.75 g) is added to it at room temperature. The mixture is stirred at 50° C. for 1 hour, during which time solid precipitate comes out from the reaction mixture. Reaction mixture is allowed to cool to room temperature and filtered under reduced pressure to obtain 3.7 g of solid complex. Complex is suspended in the biphasic mixture of ethyl acetate (20 mL) and 1 N hydrochloric acid (20 mL) and stirred for 30 to 45 min to decompose the complex. Aqueous phase is washed with 10 mL ethyl acetate. Organic phases are mixed together and washed with brine, followed by drying over sodium sulfate. Solvent is evaporated under vacuum to obtain optically pure (5)-1,1'-bi-2-naphthol (1.56 g) having 95% ee.

The acid aqueous solution which contains hydrochloride salt of (R,S)-3-[(1-phenyl ethylamino)-methyl]-hexanoic acid is neutralized with dilute solution of sodium bicarbonate to recover the (R,S)-3-[(1-phenyl ethylamino)-methyl]-hexanoic acid (0.85 g).

Example 16

Separation of (R)-1,1'-bi-2-naphthol from (RS)-1,1'-bi-2-naphthol Via Formation of Diastereomeric Co-Crystal with (R,R)-3-[(1-phenyl ethylamino)-methyl]-hexanoic acid (R,R)-3-[(1-phenyl ethylamino)-methyl]-hexanoic acid (5.0 g) is dissolved in methanol (20 mL) and (RS)-1,1'-bi-2-naphthol (5.75 g) is added to it at room temperature. The mixture is stirred at 50° C. for 1 hour, during which time solid precipitate comes out from the reaction mixture. Reaction mixture is allowed to cool to room temperature and filtered under reduced pressure to obtain 3.6 g of solid complex. Complex is suspended in the biphasic mixture of ethyl acetate (20 mL) and 1N hydrochloric acid (20 mL) and stirred for 30 to 45 min to decompose the complex. Aqueous phase is washed with 10 mL ethyl acetate. Organic phases are mixed together and washed with brine, followed by drying over sodium sulfate. Solvent is evaporated under vacuum to obtain optically pure (R)-1,1'-bi-2-naphthol (1.5 g) having 99% ee.

The acid aqueous solution which contains hydrochloride salt of (R,R)-3-[(1-phenyl ethylamino)-methyl]-hexanoic acid is neutralized with dilute solution of sodium bicarbonate to recover the (R,R)-3-[(1-phenyl ethylamino)-methyl]-hexanoic acid (0.9 g).

Example 17

Separation of (R)-1,1'-bi-2-naphthol from (RS)-1,1'-bi-2-naphthol Via Formation of Diastereomeric Co-Crystal with (S,R)-3-[(1-phenyl ethylamino)-methyl]-hexanoic acid (S,R)-3-[(1-phenyl ethylamino)-methyl]-hexanoic acid (5.0 g) is dissolved in methanol (20 mL) and (RS)-1,1'-bi-2-naphthol (5.75 g) is added to it at room temperature. The mixture is stirred at 50° C. for 1 hour, during which time solid precipitate comes out from the reaction mixture. Reaction mixture is allowed to cool to room temperature and filtered under reduced pressure to obtain 3.6 g of solid complex. Complex is suspended in the biphasic mixture of ethyl acetate (20 mL) and 1N hydrochloric acid (20 mL) and stirred for 30 to 45 min to decompose the complex. Aqueous phase is washed with 10 mL ethyl acetate. Organic phases are mixed together and washed with brine, followed by drying over sodium sulfate. Solvent is evaporated under vacuum to obtain optically pure (R)-1,1'-bi-2-naphthol (1.25 g) having 95% ee.

The acid aqueous solution which contains hydrochloride salt of (R,R)-3-[(1-phenyl ethylamino)-methyl]-hexanoic acid is neutralized with dilute solution of sodium bicarbonate to recover the (S,R)-3-[(1-phenyl ethylamino)-methyl]-hexanoic acid (0.75 g).

Example 18

Resolution of (RS)-1,1'-bi-2-naphthol Via Formation of Diastereomeric Co-Crystals by Sequential Addition of (S,S)-3-[(1-phenyl ethylamino)-methyl]-hexanoic acid and (R,R)-3-[(1-phenyl ethylamino)-methyl]-hexanoic acid (RS)-1,1'-bi-2-naphthol (5.75 g) is dissolved in methanol (20 mL) and (S,S)-3-[(1-phenyl ethylamino)-methyl]-hexanoic acid (2.5 g) is added to it at room temperature. The mixture is stirred at 50° C. for 1 hour, during which time solid precipitate comes out from the reaction mixture. Reaction mixture is allowed to cool to 5° C. and filtered under reduced pressure to obtain 4.1 g of the complex.

The complex is suspended in the biphasic mixture of ethyl acetate (20 mL) and 1N hydrochloric acid (20 mL) and stirred for 30 to 45 min to decompose the complex. Aqueous phase is washed with 10 mL ethyl acetate. Organic phases are mixed together and washed with brine, followed by drying over sodium sulfate. Solvent is evaporated under vacuum to obtain optically pure (S)-1,1'-bi-2-naphthol (2.3 g) having 99% ee (yield 80%).

The acid aqueous solution which contains hydrochloride salt of (S,S)-3-[(1-phenyl ethylamino)-methyl]-hexanoic acid is neutralized with dilute solution of sodium bicarbonate to recover the (S,S)-3-[(1-phenyl ethylamino)-methyl]-hexanoic acid (0.95 g).

(R,R)-3-[(1-phenyl ethylamino)-methyl]-hexanoic acid (2.5 g) is added to the filtrate at room temperature. The mixture is stirred at 50° C. for 1 hour, during which time solid precipitate comes out from the reaction mixture. Reaction mixture is allowed to cool to 5° C. and filtered under reduced pressure to obtain 4.8 g of solid complex. Complex is further suspended in 10 mL methanol and stirred for 1 h at 50° C. Reaction mixture is allowed to cool to room temperature and filtered under reduced pressure to obtain 4.0 g of solid complex.

The complex is suspended in the biphasic mixture of ethyl acetate (20 mL) and 1N hydrochloric acid (20 mL) and stirred for 30 to 45 min to decompose the complex. Aqueous phase is washed with 10 mL ethyl acetate. Organic phases are mixed together and washed with brine, followed by drying over sodium sulfate. Solvent is evaporated under vacuum to obtain optically pure (R)-1,1'-bi-2-naphthol (2.0 g) having 99% ee (yield 70%).

The acid aqueous solution which contains hydrochloride salt of (R,R)-3-[(1-phenyl ethylamino)-methyl]-hexanoic acid is neutralized with dilute solution of sodium bicarbonate to recover the (R,R)-3-[(1-phenyl ethylamino)-methyl]-hexanoic acid (0.8 g).

Example 19

Resolution of (RS)-1,1'-bi-2-naphthol Via Formation of Diastereomeric Co-Crystals by Sequential Addition of (R,S)-3-[(1-phenyl ethylamino)-methyl]-hexanoic acid and (S,R)-3-[(1-phenyl ethylamino)-methyl]-hexanoic acid (RS)-1,1'-bi-2-naphthol (5.75 g) is dissolved in methanol (20 mL) and (R,S)-3-[(1-phenyl ethylamino)-methyl]-hexanoic acid (2.5 g) is added to it at room temperature. The mixture is stirred at 50° C. for 1 hour, during which time solid precipitate comes out from the reaction mixture. Reaction mixture is allowed to cool to room temperature and filtered under reduced pressure to obtain 3.5 g of the complex.

The complex is suspended in the biphasic mixture of ethyl acetate (20 mL) and 1N hydrochloric acid (20 mL) and stirred for 30 to 45 min to decompose the complex. Aqueous phase is washed with 10 mL ethyl acetate. Organic phases are mixed together and washed with brine, followed by drying over sodium sulfate. Solvent is evaporated under vacuum to obtain optically pure (S)-1,1'-bi-2-naphthol (2.0 g) having 98% ee (yield 70%).

The acid aqueous solution which contains hydrochloride salt of (R,S)-3-[(1-phenyl ethylamino)-methyl]-hexanoic acid is neutralized with dilute solution of sodium bicarbonate to recover the (R,S)-3-[(1-phenyl ethylamino)-methyl]-hexanoic acid (0.8 g).

(S,R)-3-[(1-phenyl ethylamino)-methyl]-hexanoic acid (2.5 g) is then added to the filtrate at room temperature. The mixture is stirred at 50° C. for 1 hour, during which time solid precipitate comes out from the reaction mixture. Reaction mixture is allowed to cool to room temperature and filtered under reduced pressure to obtain 3.7 g of solid complex.

The complex is suspended in the biphasic mixture of ethyl acetate (20 mL) and 1N hydrochloric acid (20 mL) and stirred for 30 to 45 min to decompose the complex. Aqueous phase is washed with 10 mL ethyl acetate. Organic phases are mixed together and washed with brine, followed by drying over sodium sulfate. Solvent is evaporated under vacuum to obtain optically pure (R)-1,1'-bi-2-naphthol (1.7 g) having 98% ee (yield 65%).

The acid aqueous solution which contains hydrochloride salt of (S,R)-3-[(1-phenyl ethylamino)-methyl]-hexanoic acid is neutralized with dilute solution of sodium bicarbonate to recover the (S,R)-3-[(1-phenyl ethylamino)-methyl]-hexanoic acid (0.8 g).

Example 20

Co-Crystal Formation of 5-methyl-3-[((R)-1-phenyl-ethylamino)-methyl]-hexanoic acid with (R)-1,1'-bi-2-naphthol 5-Methyl-3-[((R)-1-phenyl-ethylamino)-methyl]-hexanoic acid (0.2 g) is dissolved in methanol (5 mL) and (R)-1,1'-bi-2-naphthol (0.25 g) is added to it at room temperature. The mixture is stirred at 50° C. for 5 h. Reaction mixture is allowed to cool to room temperature and kept over night to obtain co-crystal (0.3 g); FIG. 14. PXRD of co-crystals of (R,S)-3-[(1-phenyl ethylamino)-methyl]hexanoic acid: (S)-1,1'-bi-2-naphthol.

Example 21

Co-Crystal Formation of 5-Methyl-3-[((R)-1-phenyl-ethylamino)-methyl]-hexanoic acid with (S)-1,1'-bi-2-naphthol 5-Methyl-3-[((R)-1-phenyl-ethylamino)-methyl]-hexanoic acid (0.2 g) is dissolved in methanol (5 mL) and (S)-1,1'-bi-2-naphthol (0.25 g) is added to it at room temperature. The mixture is stirred at 50° C. for 5 h. Reaction mixture is allowed to cool to room temperature and kept over night, solvent is evaporated to obtain solid material, PXRD analysis of obtained solid shows that it is amorphous in nature.

The invention claimed is:

1. A 1:1 co-crystal of (S,S)-3-[(1-phenylethylamino)-methyl]-hexanoic acid with (S)-(−)-1,1'-bi-2-naphthol of the formula (IV)

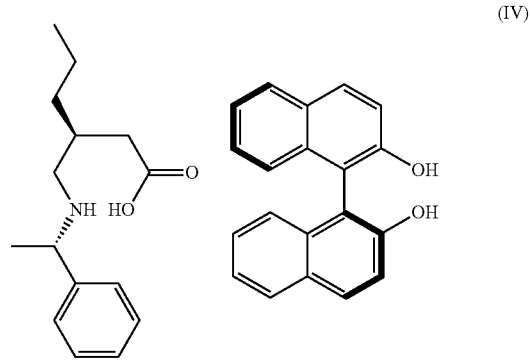

(IV)

wherein:

a) Powder X-ray diffraction peaks at the 2-theta values 9.36, 10.33, 12.17, 15.53, 17.53, 17.87, 17.96, 20.38, 21.76, 22.52, 24.47 and 27.76;

b) Differential Scanning calorimetry peak at 185° C.;

c) Specific Optical Rotation: (−)15.71° (C=1% in methanol at 25° C., λ=589 nm;

d) IR spectra (cm$^{-1}$) 3449, 3059, 2960, 2458, 1620, 1595, 1557, 1504, 1458, 1431, 1397, 1324, 1307, 1275, 1139, 1123, 818, 750 and 709;

e) Single crystal X-ray diffraction data

| Crystal system | Orthorhombic | |
|---|---|---|
| Space group | P212121 | |
| Unit cell dimensions | a = 10.1158(18) Å | alpha = 90 deg. |
| | b = 11.293(2) Å | beta = 90 deg. |
| | c = 26.118(5) Å | gamma = 90 deg |
| Volume | 2983.8(9) Å$^3$ | |
| Z | 4 | |
| Density (calculated) | 1.192 g/cm$^3$. | |

2. A 1:1 co-crystal of (R,R)-3-[(1-phenylethylamino)-methyl]-hexanoic acid with (R)-(+)-1,1'-bi-2-naphthol of the formula (V)

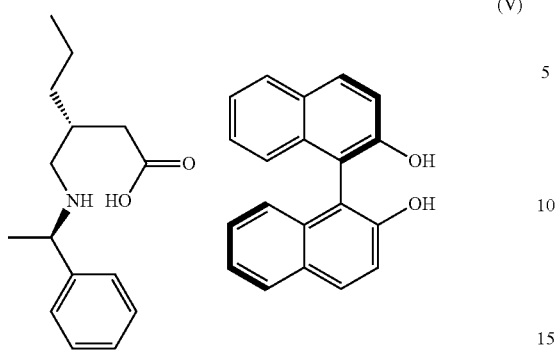

(V)

wherein:
a) Powder X-ray diffraction peaks at the 2-theta values: 9.34, 10.35, 12.18, 15.51, 15.66, 17.04, 17.55, 17.86, 18.24, 18.67, 19.19, 20.37, 20.62, 21.54, 21.76, 22.54, 23.55, 24.53 and 27.24;
b) Differential Scanning calorimetry peak at 186° C.;
c) Specific Optical Rotation: (+) 16.44° (C=1% in methanol at 25° C., λ=589 nm); and
d) IR Spectra (cm$^{-1}$) 3449, 3059, 2960, 2458, 1620, 1595, 1557, 1504, 1458, 1431, 1397, 1324, 1307, 1275, 1139, 1123, 818, 750 and 709.

3. A method of resolution of racemic (RS)-1,1'-bi-2-naphthol (I) through a formation of co-crystal of formula (IV) and (V) with respective co-crystal former of the formula (II) and (III) to give optically pure (S)-(−)-1,1'-bi-2-naphthol and (R)-(+)-1,1'-bi-2-naphthol respectively;

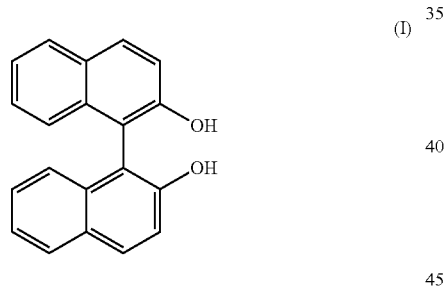

(I)

comprising of
a) Reaction of (RS)-1,1'-bi-2-naphthol of formula (I) with compound of formula (II) to obtain co-crystal of formula (IV) in methanol at 50° C. by employing molar ratio of 0.5 to 1.5 of compound of formula (I) to compound of formula (II);

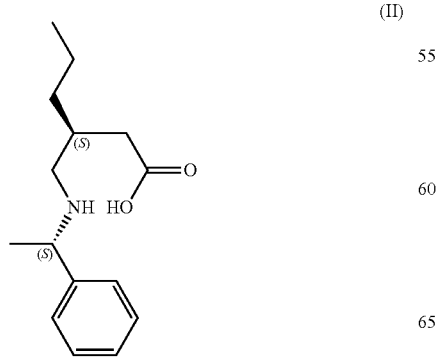

(II)

b) Separation of co-crystal of formula (IV) obtained at step a) by filtration;
c) Decomposition of the co-crystal of formula (IV) obtained at the step b in biphasic dilute aqueous hydrochloric acid-ethyl acetate to obtain the optically pure (S)-(−)-1,1'-bi-2-naphthol from ethyl acetate layer;
d) Recovery of compound of formula (II) from aqueous layer obtained at the step c) by neutralizing with sodium bicarbonate; e) Reaction of mother liquor obtained at step b) containing the other antipode of compound of formula (I), with compound of formula (III) at 50° C. to give co-crystal of formula (V) by employing molar ratio of 0.5 to 1.5 of compound of formula (I) to the compound of formula (III);

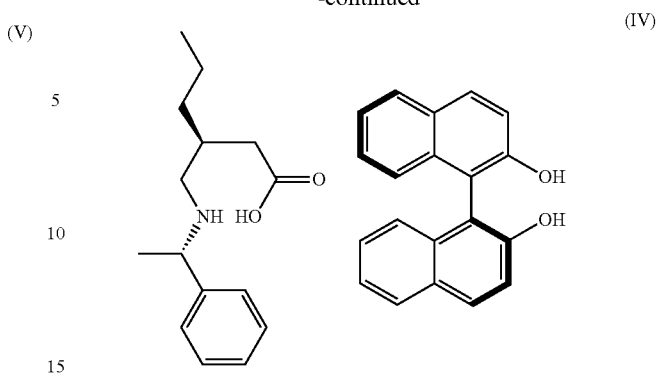

(IV)

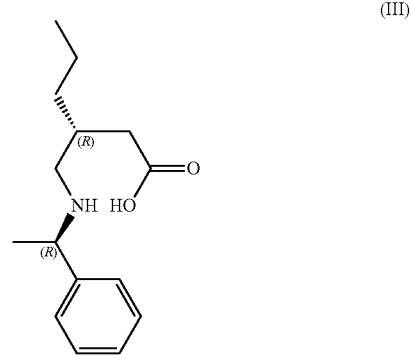 [SMILES: CCC[C@@H](CN[C@H](C)c1ccccc1)CC(=O)O]

(III)

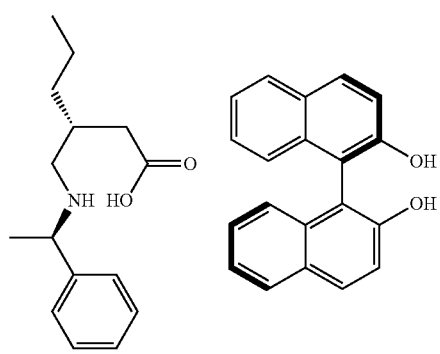

(V)

f) Separation of co-crystal of formula (V) obtained at step d) by filtration;
g) Decomposition of the co-crystal of formula (V) obtained in the step d) in biphasic mixture of dilute aqueous hydrochloric acid-ethyl acetate to obtain the optically pure (R)-(+)-1,1'-bi-2-naphthol from ethyl acetate layer; and h) Recovery of compound of formula (III) from aqueous layer obtained at the step g), by neutralizing with sodium bicarbonate.

4. A method of resolution of racemic (RS)-1,1'-bi-2-naphthol (I) through a formation of co-crystal of formula (V) and (IV) with respective co-crystal former of the formula (III) and (II) to give optically pure (R)-(+)-1,1'-bi-2-naphthol and (S)-(−)-1,1'-bi-2-naphthol respectively; comprising of a) Reaction of (RS)-1,1'-bi-2-naphthol of formula (I) with compound of the formula of (III) to give co-crystal of formula (V) in methanol at 50° C. by employing molar ratio of 0.5 to 1.5 of compound of formula (I) to the compound of formula (III);

(III)

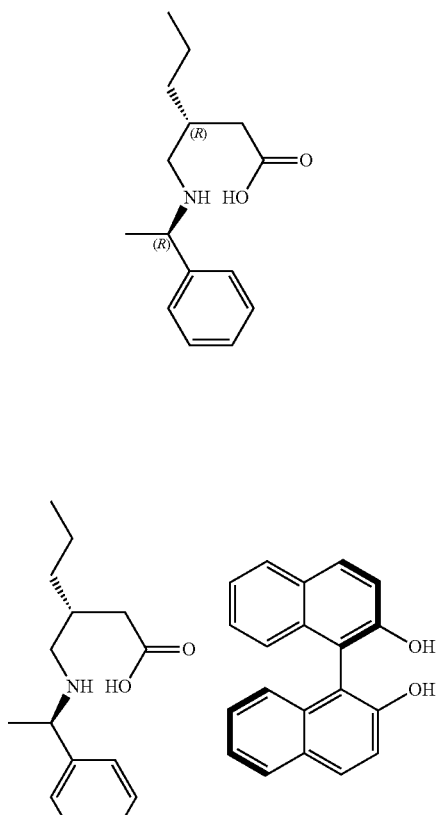

(V)

b) Separation of co-crystal of formula (V) obtained at step (a) by filtration;
c) Decomposition of the co-crystal of formula (V) obtained at the step b) in biphasic mixture of dilute aqueous hydrochloric acid-ethyl acetate to obtain the optically pure (R)-(+)-1,1'-bi-2-naphthol from ethyl acetate layer;
d) Recovery of compound of formula (III) from aqueous layer obtained at the step c) by neutralizaing with sodium bicarbonate;
e) Reaction of mother liquor obtained at step b) containing the other antipode of compound of formula (I), with compound of formula (II) at 50° C. to give co-crystal of formula (IV) by employing molar ratio of 0.5 to 1.5 of compound of formula (I) to the compound of formula (II);

(II)

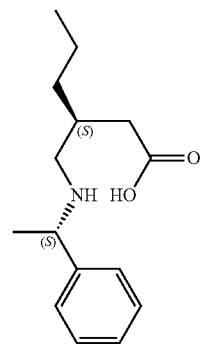

(IV)

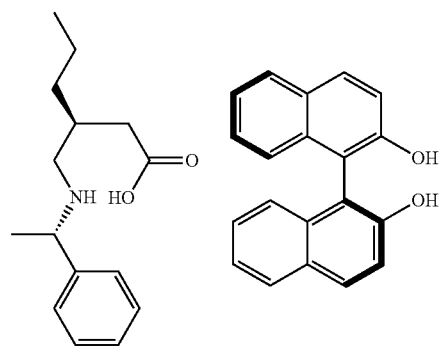

f) Separation of co-crystal of formula of (IV) obtained at step d) by filtration;
g) Decomposition of the co-crystal obtained in the step d) in biphasic mixture of dilute aqueous hydrochloric acid to obtain the optically pure (S)-(−)-1,1'-bi-2-naphthol from ethyl acetate layer; and
h) Recovery of compound of formula (II) from aqueous layer obtained at the step g) by neutralizing with sodium bicarbonate.

5. A 1:1 co-crystal of (R,S)-3-[(1-phenylethylamino)-methyl]-hexanoic acid with (S)-(−)-1,1'-bi-2-naphthol of the formula (VIII)

(VIII)

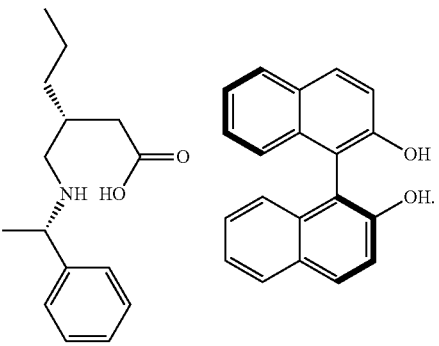

wherein:
a) Powder X-ray diffraction peaks at the 2-theta values 9.38, 10.35, 12.23, 15.44, 15.51, 17.60, 17.87, 19.30, 20.45, 21.66, 22.57, 24.41, 24.69 and 28.48;
b) Differential Scanning calorimetry peak at 177° C.;
c) Specific optical rotation angle: (−)18.46° (C=1% in methanol at 25° C., λ=589 nm);
d) IR spectra (cm$^{-1}$): 3449, 3059, 2960, 2458, 1620, 1595, 1557, 1504, 1458, 1431, 1397, 1324, 1307, 1275, 1139, 1123, 818, 750 and 709;
e) Single crystal X-ray diffraction data:

| Crystal system | Orthorhombic | |
|---|---|---|
| Space group | | P212121 |
| Unit cell dimensions | a = 10.039 Å | alpha = 90 deg. |
| | b = 11.18 Å | beta = 90 deg. |
| | c = 26.35 Å | gamma = 90 deg |
| Volume | | 2958.132 Å$^3$ |
| Z | | 4 |
| Density (calculated) | | 1.2 g/cm$^3$. |

6. A 1:1 co-crystal of (S,R)-3-[(1-phenylethylamino)-methyl]-hexanoic acid with (R)-(+)-1,1'-bi-2-naphthol of the formula (IX)

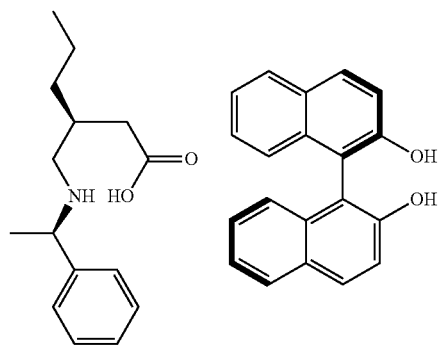

(IX)

wherein:
a) Powder X-ray diffraction peaks at the 2-theta values 9.25, 10.31, 12.23, 15.44, 15.51, 17.60, 17.87, 19.30, 20.45, 21.66, 22.57, 24.41, 24.69 and 28.48;
b) Differential scanning calorimetry peak at 172° C.;
c) Specific optical rotation: (+) 19.97° (C=1% in methanol at 25° C., λ=589 nm) and
d) IR Spectra (cm$^{-1}$): 3449, 3059, 2960, 2458, 1620, 1595, 1557, 1504, 1458, 1431, 1397, 1324, 1307, 1275, 1139, 1123, 818, 750 and 709.

7. A method of resolution of racemic (RS)-1,1'-bi-2-naphthol (I) through a formation of co-crystal of formula (VIII) and (IX) with respective co-crystal former of the formula (VI) and (VII) to give optically pure (S)-(−)-1,1'-bi-2-naphthol and (R)-(+)-1,1'-bi-2-naphthol respectively;

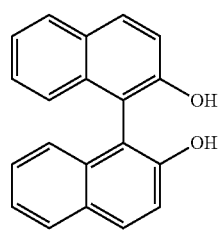

[I]

comprising of
a) Reaction of (RS)-1,1'-bi-2-naphthol of formula (I) compound of formula (VI) to obtain co-crystal of formula (VIII) in methanol at 50° C. by employing molar ratio of 0.5 to 1.5 of compound of formula (I) to the compound of formula (VI);

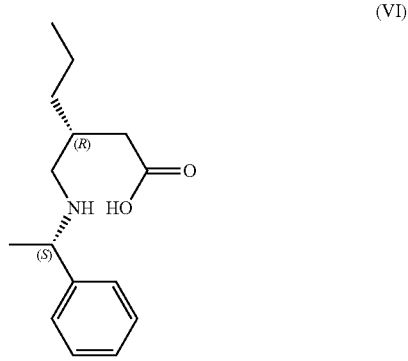 [SMILES: CCC[C@@H](CN[C@@H](C)c1ccccc1)CC(=O)O]

(VI)

(VIII)

b) Separation of co-crystal of formula (VIII) obtained at step a) by filtration;
c) Decomposition of the co-crystal of formula of (VIII) obtained at the step b) in biphasic mixture of dilute aqueous hydrochloric acid-ethyl acetate to obtain the optically pure (S)-(−)-1,1'-bi-2-naphthol from ethyl acetate layer;
d) Recovery of compound of formula (VI) from aqueous layer obtained at the step c) by neutralizing with sodium bicarbonate;
e) Reaction of mother liquor obtained at step b) containing the other antipode of compound of formula (I), with compound of formula (VII) at 50° C. to yield co-crystal of formula (IX) by employing molar ratio of 0.5 to 1.5 of compound of formula (I) to the compound of formula (VII);

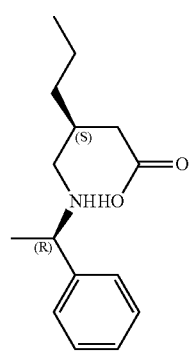

(VII)

-continued

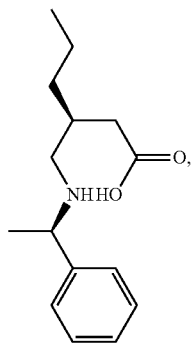 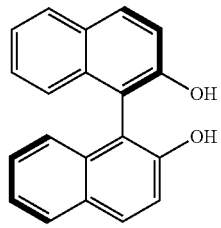

(IX)

f) Separation of co-crystal of formula (IX) obtained at step d) by filtration;
g) Decomposition of the co-crystal of formula of (IX) obtained in the step d) in biphasic mixture of dilute aqueous hydrochloric acid-ethyl acetate to obtain the optically pure (R)-(+)-1,1'-bi-2-naphthol from ethyl acetate layer; and
h) Recovery of compound of formula (VII) from aqueous layer obtained at the step g) by neutralizing with sodium bicarbonate.

8. A method of resolution of racemic (RS)-1,1'-bi-2-naphthol (I) through a formation of co-crystal of formula (IX) and (VIII) with respective co-crystal former of the formula (VII) and (VI) to give optically pure (R)-(+)-1,1'-bi-2-naphthol and (S)-(−)-1,1'-bi-2-naphthol respectively;
    a) Reaction of (RS)-1,1'-bi-2-naphthol of formula (I) compound of the formula (VII) to obtain co-crystal of formula (IX) in methanol at 50° C. by employing molar ratio of 0.5 to 1.5 of compound of formula (I) to the compound of formula (VII);

(VII)

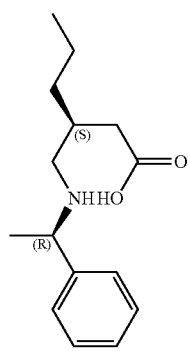

-continued

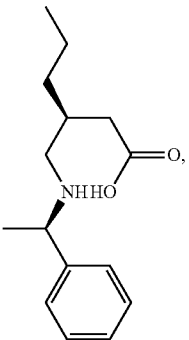 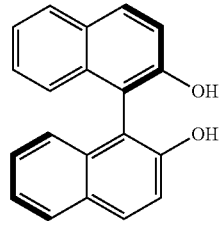

(IX)

b) Separation of co-crystal of formula (IX) obtained at step a) by filtration;
c) Decomposition of the co-crystal of formula (IX) obtained at the step b) in biphasic mixture of dilute aqueous hydrochloric acid-ethyl acetate to obtain the optically pure (R)-(+)-1,1'-bi-2-naphthol from ethyl acetate layer;
d) Recovery of compound of formula (VII) from aqueous layer obtained at the step c) by neutralizing with sodium bicarbonate;
e) Reaction of mother liquor obtained at step b) containing the other antipode of compound of formula (I), with compound of formula (VI) at 50° C. to yield co-crystal of formula (VIII) by employing molar ratio of 0.5 to 1.5 of compound of formula (I) to the compound of formula (VI);

(VI)

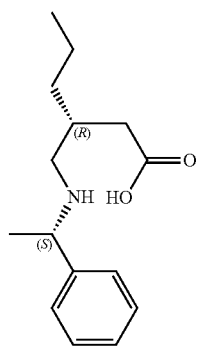

(VIII)

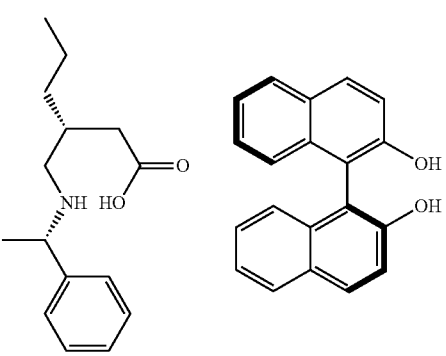

f) Separation of co-crystal of formula of (VIII) obtained at step d) by filtration;
g) Decomposition of the co-crystal obtained in the step d) in biphasic mixture of dilute aqueous hydrochloric acid-ethyl acetate to obtain the optically pure (S)-(−)-1,1'-bi-2-naphthol from ethyl acetate layer; and h) Recovery of compound of formula (VI) from aqueous layer obtained at the step g) by neutralizing with sodium bicarbonate.

* * * * *